US011472863B2

(12) United States Patent
Gao et al.

(10) Patent No.: US 11,472,863 B2
(45) Date of Patent: Oct. 18, 2022

(54) HUMAN COAGULATION FACTOR IX (FIX) FUSION PROTEIN, PREPARATION METHOD THEREFOR, AND USE THEREOF

(71) Applicants: AMPSOURCE BIOPHARMA SHANGHAI INC., Shanghai (CN); PHARMAB, INC., Shanghai (CN)

(72) Inventors: YongJuan Gao, Shanghai (CN); Si Chen, Shanghai (CN); Zirui Li, Shanghai (CN); Xiaoping Tu, Shanghai (CN); Bill Nai-chau Sun, Shanghai (CN); Qiang Li, Shanghai (CN)

(73) Assignees: Ampsource Biopharma Shanghai Inc., Shanghai (CN); Pharmab, Inc., Shanghai (CN)

(*) Notice: Subject to any disclaimer, the term of this patent is extended or adjusted under 35 U.S.C. 154(b) by 23 days.

(21) Appl. No.: 16/604,081

(22) PCT Filed: Apr. 10, 2017

(86) PCT No.: PCT/CN2017/079872
§ 371 (c)(1),
(2) Date: Oct. 9, 2019

(87) PCT Pub. No.: WO2018/032786
PCT Pub. Date: Feb. 22, 2018

(65) Prior Publication Data
US 2020/0157185 A1    May 21, 2020

(30) Foreign Application Priority Data

Aug. 19, 2016  (CN) .......................... 201610694914.1

(51) Int. Cl.
| | | |
|---|---|---|
| A61K 38/00 | (2006.01) | |
| C07K 14/745 | (2006.01) | |
| C07K 14/59 | (2006.01) | |
| C07K 14/76 | (2006.01) | |
| C07K 14/79 | (2006.01) | |
| C12N 5/10 | (2006.01) | |
| C12N 15/62 | (2006.01) | |
| C12N 15/85 | (2006.01) | |
| C07K 14/50 | (2006.01) | |
| C07K 14/65 | (2006.01) | |

(52) U.S. Cl.
CPC ............ *C07K 14/745* (2013.01); *C07K 14/50* (2013.01); *C07K 14/59* (2013.01); *C07K 14/65* (2013.01); *C07K 14/76* (2013.01); *C07K 14/79* (2013.01); *C12N 5/10* (2013.01); *C12N 15/62* (2013.01); *C12N 15/85* (2013.01); *A61K 38/00* (2013.01); *C07K 2317/732* (2013.01); *C07K 2317/734* (2013.01); *C07K 2319/30* (2013.01); *C07K 2319/31* (2013.01)

(58) Field of Classification Search
CPC ... A61K 38/18; A61P 3/04; A61P 3/06; A61P 3/10; C07K 14/59; C07K 14/745; C07K 14/76; C07K 14/79; C07K 2317/732; C07K 2317/734; C07K 2319/30; C07K 2319/31; C07K 14/00; C07K 2319/00; C12N 15/62

See application file for complete search history.

(56) References Cited

U.S. PATENT DOCUMENTS

| | | |
|---|---|---|
| 4,399,216 A | 8/1983 | Axel et al. |
| 4,818,679 A | 4/1989 | Chasin et al. |
| 6,103,501 A | 8/2000 | Boime et al. |
| 6,225,449 B1 | 5/2001 | Boime |
| 7,189,827 B2 | 3/2007 | Feige |
| 7,582,607 B2 | 9/2009 | Frye et al. |
| 8,163,889 B2 | 4/2012 | Kim et al. |
| 8,273,854 B2 | 9/2012 | Glaesner et al. |
| 8,304,224 B2 | 11/2012 | Lovgren |
| 8,476,234 B2 | 7/2013 | Fima et al. |
| 9,023,791 B2 | 5/2015 | Boettcher et al. |
| 9,266,935 B2 | 2/2016 | Boettcher et al. |
| 9,279,013 B2 | 3/2016 | Walker et al. |

(Continued)

FOREIGN PATENT DOCUMENTS

| | | |
|---|---|---|
| CN | 1290301 A | 4/2001 |
| CN | 1889937 A | 1/2007 |

(Continued)

OTHER PUBLICATIONS

Machine generated English language translation of CN106279437A—Obtained from google patents and accessed on Aug. 7, 2020 at https://patents.google.com/patent/CN106279437A/en?oq=CN+106279437A+ (Year: 2017).*
Chinese Office Action for Application No. 201610692679.4 dated Dec. 27, 2016.
International Search Report for Application No. PCT/CN2016/106011 dated Feb. 17, 2017.
International Search Report for Application No. PCT/CN2017/079871 dated Jun. 2, 2017.
Chinese Office Action for Application No. 201780000362.2 dated Jul. 11, 2019.

(Continued)

*Primary Examiner* — Aradhana Sasan
*Assistant Examiner* — Mercy H Sabila
(74) *Attorney, Agent, or Firm* — Jenkins, Wilson, Taylor & Hunt, P.A.

(57) ABSTRACT

A hyperglycosylated recombinant human coagulation factor IX (FIX) fusion protein, a preparation method therefor, and use thereof. The fusion protein sequentially comprises, from N- to C-terminus, a human FIX, a flexible peptide linker, at least one human chorionic gonadotropin β subunit carboxy-terminal peptide rigid unit, and a half-life extending moiety. The fusion protein has a biological activity similar to that of the recombinant FIX, an extended in vivo activity half-life, and reduced immunogenicity, so as to improve pharmacokinetics and pharmacodynamics.

8 Claims, 3 Drawing Sheets

Specification includes a Sequence Listing.

(56) References Cited

U.S. PATENT DOCUMENTS

| | | |
|---|---|---|
| 9,493,543 B2 | 11/2016 | Bolt et al. |
| 9,573,987 B2 | 2/2017 | Dimarchi et al. |
| 9,580,483 B2 | 2/2017 | Ling et al. |
| 9,675,676 B2 | 6/2017 | Pierce et al. |
| 9,803,023 B2 | 10/2017 | Chamberlain et al. |
| 9,867,873 B2 | 1/2018 | Pierce et al. |
| 9,915,665 B2 | 3/2018 | Benatuil et al. |
| 10,010,622 B2 | 7/2018 | Dumont et al. |
| 10,023,624 B2 | 7/2018 | Hou et al. |
| 10,287,564 B2 | 5/2019 | Hong et al. |
| 2001/0012628 A1 | 8/2001 | Agarwal et al. |
| 2003/0211580 A1 | 11/2003 | Lustbader |
| 2005/0250185 A1 | 11/2005 | Murphy et al. |
| 2007/0129298 A1 | 6/2007 | Krebber et al. |
| 2009/0042784 A1 | 2/2009 | Krarup |
| 2010/0081614 A1 | 4/2010 | Fares et al. |
| 2013/0108629 A1 | 5/2013 | Dumont et al. |
| 2013/0202596 A1 | 8/2013 | Salas et al. |
| 2013/0252884 A1 | 9/2013 | Garibay et al. |
| 2013/0274194 A1 | 10/2013 | Dumont et al. |
| 2013/0281671 A1 | 10/2013 | Peters et al. |
| 2014/0294821 A1 | 10/2014 | Dumont et al. |
| 2014/0303084 A1 | 10/2014 | Thorn et al. |
| 2014/0308280 A1 | 10/2014 | Maloney et al. |
| 2014/0357843 A1 | 12/2014 | Oh et al. |
| 2014/0370035 A1 | 12/2014 | Jiang et al. |
| 2014/0378663 A1 | 12/2014 | Fontayne et al. |
| 2015/0079072 A1 | 3/2015 | Sommer et al. |
| 2015/0185235 A1 | 7/2015 | Sommer |
| 2015/0191526 A1 | 7/2015 | Low et al. |
| 2015/0203558 A1 | 7/2015 | Fares et al. |
| 2015/0266943 A1 | 9/2015 | Chhabra et al. |
| 2015/0353911 A1* | 12/2015 | Salas ............... A61K 47/62 424/94.64 |
| 2016/0000884 A1 | 1/2016 | Rischel et al. |
| 2016/0115467 A1 | 4/2016 | Salas |
| 2016/0296607 A1 | 10/2016 | Jiang |
| 2019/0184026 A1 | 6/2019 | Li et al. |
| 2019/0365867 A1 | 12/2019 | Li et al. |

FOREIGN PATENT DOCUMENTS

| | | |
|---|---|---|
| CN | 101010338 A | 8/2007 |
| CN | 1802386 B | 12/2010 |
| CN | 102625811 A | 8/2012 |
| CN | 102639144 A | 8/2012 |
| CN | 102802657 A | 11/2012 |
| CN | 103140237 A | 6/2013 |
| CN | 103328502 A | 9/2013 |
| CN | 103539860 A | 1/2014 |
| CN | 103539861 A | 1/2014 |
| CN | 103539868 A | 1/2014 |
| CN | 103539869 A | 1/2014 |
| CN | 103649127 A | 3/2014 |
| CN | 103827142 A | 5/2014 |
| CN | 103897064 A | 7/2014 |
| CN | 103945871 A | 7/2014 |
| CN | 104039831 B | 9/2014 |
| CN | 104114183 A | 10/2014 |
| CN | 104427994 A | 3/2015 |
| CN | 104519897 A | 4/2015 |
| CN | 104519912 A | 4/2015 |
| CN | 104693270 A | 6/2015 |
| CN | 104774269 A | 7/2015 |
| CN | 104903352 A | 9/2015 |
| CN | 105153313 A | 12/2015 |
| CN | 103897064 B | 5/2016 |
| CN | 105753945 A | 7/2016 |
| CN | 104024273 B | 10/2016 |
| CN | 106117370 A | 11/2016 |
| CN | 106256835 A | 12/2016 |
| CN | 106279436 A | 1/2017 |
| CN | 106279437 A | 1/2017 |
| CN | 106317226 A | 1/2017 |
| CN | 106117370 B | 5/2017 |
| CN | 106279437 B | 10/2017 |
| CN | 107474138 A | 12/2017 |
| CN | 105753945 B | 4/2019 |
| CN | 110028587 A | 7/2019 |
| CN | 108137708 B | 10/2019 |
| CN | 110229238 B | 10/2020 |
| EA | 005404 B1 | 2/2005 |
| EA | 201291480 A1 | 9/2013 |
| EP | 1 624 891 B1 | 8/2009 |
| EP | 2822576 B1 | 1/2018 |
| EP | 2808343 B1 | 5/2019 |
| EP | 3 502 143 A1 | 6/2019 |
| EP | 3 620 474 A1 | 3/2020 |
| JP | 2014-522838 A | 9/2014 |
| JP | 2019-531087 A | 10/2019 |
| KR | 2010-0099179 A | 9/2010 |
| KR | 10-1027427 B1 | 4/2011 |
| KR | 20190042629 A | 4/2019 |
| RU | 2312868 C2 | 12/2007 |
| WO | WO 03/011213 A2 | 2/2003 |
| WO | WO 03/061712 A1 | 7/2003 |
| WO | WO 2004/110472 A2 | 12/2004 |
| WO | WO 2005/000892 A2 | 1/2005 |
| WO | WO 2005/058953 A2 | 6/2005 |
| WO | WO 2005/091944 A2 | 10/2005 |
| WO | WO 2005/113606 A2 | 12/2005 |
| WO | WO 2006/028595 A2 | 3/2006 |
| WO | WO 2006/028714 A1 | 3/2006 |
| WO | WO 2006/050247 A2 | 5/2006 |
| WO | WO 2006/053301 A2 | 5/2006 |
| WO | WO 2006/065582 A2 | 6/2006 |
| WO | WO 2007/090584 A1 | 8/2007 |
| WO | WO 2008/121563 A2 | 10/2008 |
| WO | WO 2009/149171 A2 | 12/2009 |
| WO | WO 2010/042747 A2 | 4/2010 |
| WO | WO 2010/084169 A2 | 7/2010 |
| WO | WO 2010/129503 A1 | 11/2010 |
| WO | WO 2010/129600 A2 | 11/2010 |
| WO | WO 2010/142665 A1 | 12/2010 |
| WO | WO 2011/071783 A1 | 6/2011 |
| WO | WO 2011/092234 A1 | 8/2011 |
| WO | WO 2011/130417 A2 | 10/2011 |
| WO | WO 2012/010553 A1 | 1/2012 |
| WO | WO 2012/066075 A1 | 5/2012 |
| WO | WO 2012/158704 A1 | 11/2012 |
| WO | WO 2012/170438 A2 | 12/2012 |
| WO | WO 2012/175751 A2 | 12/2012 |
| WO | WO 2013/049234 A2 | 4/2013 |
| WO | WO 2013/049247 A1 | 4/2013 |
| WO | WO 2013/096386 A1 | 6/2013 |
| WO | WO 2013/100702 A1 | 7/2013 |
| WO | WO 2013/121416 | 8/2013 |
| WO | WO 2013/152351 A2 | 10/2013 |
| WO | WO 2013/185114 A2 | 12/2013 |
| WO | WO 2013/188181 A1 | 12/2013 |
| WO | WO 2014/026954 A1 | 2/2014 |
| WO | WO 2014/037373 A1 | 3/2014 |
| WO | WO-2014052490 A1 * | 4/2014 ........... C07K 14/745 |
| WO | WO 2014/106015 A2 | 7/2014 |
| WO | WO 2015/062350 A1 | 5/2015 |
| WO | WO 2016/114633 A1 | 7/2016 |
| WO | WO 2017/074123 A1 | 5/2017 |
| WO | WO 2018/032637 A1 | 2/2018 |
| WO | WO 2018/032638 A1 | 2/2018 |
| WO | WO 2018/032785 A1 | 2/2018 |
| WO | WO 2018/32786 A1 | 2/2018 |

OTHER PUBLICATIONS

Japanese Office Action for Application No. 2019-530527 dated Mar. 31, 2020.
Collins et al., "Recombinant long-acting glycoPEGylated factor IX in hemophilia B: a multinational randomized phase 3 trial," Blood, vol. 124, No. 26, pp. 3880-3886 (2014).
Coyle et al., "An open-label phase I study to evaluate the pharmacokinetics and safety profile of Bay 94-9027, a PEGylated B-domain-deleted recombinant factor VIII, in previously treated patients with

(56) References Cited

OTHER PUBLICATIONS severe hemophilia A," Haemophilia, vol. 18 (Suppl. 3), FP-MO-03.2-3, p. 22 (2012).
Coyle et al., "Phase I study of BAY 94-9027, a PEGylated B-domain-deleted recombinant factor VIII with an extended half-life, in subjects with hemophilia A," Journal of Thrombosis and Haemostasis, vol. 12, pp. 488-496 (2014).
Datta-Mannan et al., "Influence of improved FcRn binding on the subcutaneous bioavailability of monoclonal antibodies in cynomolgus monkeys," mAbs, vol. 4, No. 2, pp. 267-273 (2012).
Dumont et al., "Prolonged activity of a recombinant factor VIII-Fc fusion protein in hemophilia A mice and dogs," Blood, vol. 119, No. 13, pp. 3024-3030 (2012).
Fares et al., "Design of a long-acting follitropin agonist by fusing the C-terminal sequence of the chorionic gonadotropin β subunit to the follitropin β subunit," Proc. Natl. Acad. Sci. USA, vol. 89, pp. 4304-4308 (1992).
Gilbert et al., "Specific Membrane Binding of Factor VIII Is Mediated by 0-Phospho-$_L$-serine, a Moiety of Phosphatidylserine," Biochemistry, vol. 32, pp. 9577-9585 (1993).
Hinton et al., "Engineered Human IgG Antibodies with Longer Serum Half-lives in Primates," The Journal of Biological Chemistry, vol. 279, No. 8, pp. 6212-6216 (2004).
Hinton et al., "An Engineered Human IgG1 Antibody with Longer Serum Half-Life," The Journal of Immunology, vol. 176, pp. 346-356 (2006).
Jefferis et al., "IgG-Fc-mediated effector functions: molecular definition of interaction sites for effector ligands and the role of glycosylation," Immunol. Rev., vol. 163, pp. 59-76 (1998).
Li et al., "Design of Linker Peptides and Its Application in Fusion Protein," Journal of Food Science and Biotechnology, vol. 34, No. 11, pp. 1121-1127 (2015).
McCue et al., "Manufacturing process used to produce long-acting recombinant factor VIII Fc fusion protein," Biologicals, vol. 43, pp. 213-219 (2015).
Peters et al., "Prolonged activity of factor IX as a monomeric Fc fusion protein," Blood, vol. 115, No. 10, pp. 2057-2064 (2010).
Peters et al., "Biochemical and functional characterization of a recombinant monomeric factor VIII-Fc fusion protein," Jounral of Thrombosis and Haemostasis, vol. 11, pp. 132-141 (2012).
Powell et al., "Safety and prolonged activity of recombinant factor VIII Fc fusion protein in hemophilia A patients," Blood, vol. 119, No. 13, pp. 3031-3037 (2012).
Roopenian et al., "FcRn: the neonatal Fc receptor comes of age," Nat. Rev. Immunol., vol. 7, No. 9, pp. 715-725 (2007).
Sambrook et al., Molecular Cloning: A Laboratory Manual, Second Edition, vol. 1, Cold Spring Harbor Laboratory Press (1989).
Shields et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 276, No. 9, pp. 6591-6604 (2001).
Tiede et al., "Enhancing the pharmacokinetic properties of recombinant factor VIII: first-in-human trial of glycoPEGylated recombinant factor VIII in patients with hemophilia A," Journal of Thrombosis and Haemostasis, vol. 11, pp. 670-678 (2013).
Turecek et al., "BAX 855, a PEGylated rFVIII product with prolonged half-life," Hämostaseologie, Vo. 32 (Suppl. 1), pp. S29-S38 (2012).
Chinese Office Action for Application No. 201610692838.0 dated May 31, 2017.
Written Opinion and International Search Report for Application No. PCT/CN2017/079872 dated Jul. 5, 2017.
International Preliminary Report on Patentability, Written Opinion, and International Search Report for Application No. PCT/CN2016/106010 dated Feb. 19, 2019.
Arai et al., "Design of the linkers which effectively separate domains of a bifunctional fusion protein", Protein Engineering, vol. 14, No. 8, pp. 529-532 (2001).
Beenken et al., "The FGF family: biology, pathophysiology and therapy", Nature Reviews Drug Discover, vol. 8, pp. 235 (2009).

Berglund et al., "Fibroblast Growth Factor 21 Controls Glycemia via Regulator of Hepatic Glucose Flux and insulin Sensitivity", Endocrinology, vol. 150, pp. 4084-4093 (2009).
Broze et al., "Purification and Properties of Human Coagulation Factor VII", The Journal of Biological Chemistry, vol. 255, No. 4, pp. 1242-1247 (1980).
Calo et al., "Enhancing the longevity and in vivo potency of therapeutic proteins: The power of CTP," Precision Medicine, vol. 2, Edition 989, (Sep. 30, 2015).
Chen et al., Fusion protein linkers: property, design and functionality, Advanced drug delivery reviews, vol. 65, No. 10, pp. 1357-1369 (2013).
Coskun et al., "Fibroblast Growth Factor 21 Corrects Obesity in Mice" Endocrinology, vol. 149, pp. 6018-6027 (2008).
Dickneite et al., "Prothrombin complex concentrate versus recombinant factor VIIa for reversal of coumarin anticoagulation", Thrombosis Research, vol. 119, pp. 643-651 (2007).
Dong et al., "Pharmacokinetics and pharmacodynamics of PF-05231023, a novel long-acting FGF21 mimetic, in a first-in-human study", British Journal of Clinical Pharmacology, vol. 80, pp. 1051-1063 (2015).
Dutchak et al.. "Fibroblast Growth Factor-21 Regulates PPAR Activity and the Antidiabetic Actions of Thiazolidinediones", Cell, vol. 148, pp. 556-567 (2012).
Gaich et al., "The Effects of LY2405319, an FGF21 Analog, in Obese Human Subjects with Type 2 Diabetes", Cell Metabolism, vol. 18, pp. 333-340 (2013).
Golor et al., "Safety and pharmacokinetics of a recombinant fusion protein linking coagulation factor VIIa with albumin in healthy volunteers", Journal of Thrombosis and Haemostasis, vol. 11, pp. 1977-1985 (2013).
Hagen et al., "Characterization of a cDNA coding for human factor VII", Proc. Natl. Acad. Sci. vol. 83, pp. 2412-2416 (1986).
Hart et al., "Acquired Hemophilia", Haemophilia, vol. 18, Suppl. 3, pp. 1-208 (2012).
Hecht et al., "Rationale-Based Engineering of a Potent Long-Acting FGF21 Analog for the Treatment of Type 2 Diabetes", Plos One, vol. 7, Issue 11, pp. e49345 (2012).
Hedner et al., "Use of human factor VIIa in the treatment of two hemophilia A patients with high-titer inhibitors", The Jornal of Clinical Investigstion, vol. 71, pp. 1836-1841 (1983).
Kharitonenkov et al., "FGF-21 as a novel metabolic regulator", The Journal of Clinical Investigation, vol. 115, No. 6, pp. 1627-1635 (2005).
Kharitonenkov et al., "The Metabolic State of Diabetic Monkeys Is Regulated by Fibroblast Growth Factor-21", Endocrinology, vol. 148, pp. 774-781 (2007).
Kisiel et al., "Enzymological aspects of blood coagulation", Behring Institute Mitleilungen, vol. 73, pp. 29-42 (1983).
Klein et al., "Design and characterization of structured protein linkers with different flexibilities", Protein Engineering, Design and Selection, vol. 27, No. 10, pp. 325-330 (Oct. 1, 2014).
Knudsen, Lotte Bjerre, "Glucagon-like Peptide-1: The Basis of a New Class of Treatment for Type 2 Diabetes", Journal of Medicinal Chemistry, vol. 47, No. 17, pp. 4128-4134 (2004).
Li et al., "Construction of a linker library with widely controllable flexibility for fusion protein design", Appl. Microbiol Biotechnology, vol. 100, pp. 215-225, (2016).
Lin et al., "Fibroblast Growth Factor 21 Prevents Atherosclerosis by Suppression of Hepatic Sterol Regulatory Element-Binding Protein-2 and Induction of Adiponectin in Mice", Circulation, vol. 131, pp. 1861-1871 (2015).
Ljung et al., "40K glycoPEGylated, recombinant FVIIa: 3-month, double-blind, randomized trial of safety, pharmacokinetics and preliminary efficacy in hemophilia patients with inhibitors", Journal of Thrombosis and Haemostasis, vol. 11, pp. 1260-1268 (2013).
Luo et al., "Flexibility between the Protease and Helicase Domains of the Dengue Virus NS3 Protein Conferred by the Linker Region and Its Functional Implications", The Journal of Biological Chemistry, vol. 285, No. 24, pp. 18817-18827 (2010).
Maeda et al., Engineering of functional chimeric protein G-Vargula Luciferase, Analytical biochemistry, vol. 249, No. 2, pp. 147-152 (1997).

(56) References Cited

OTHER PUBLICATIONS

Micanovic et al., "Different Roles of N- and C-Termini in the Functional Activity of FGF21" Journal of cellular physiology, vol. 219, pp. 227-234 (2009).
Moore et al., "Particular fibroblast growth factors function as metabolic hormones and act through a certain signaling cascade design to control specific states of homeostasis", Science, vol. 316, pp. 1436-1438 (2007).
Neidigh et al., "Exendin-4 and Glucagon-like-peptide-1: NMR Structural Comparisons in the Solution and Micelle-Associated States", Biochemistry 2001, 40, 13188-13200 (2001).
Orlando M., Modification of proteins and low molecular weight substance with hydroxyethyl starch (HES), Inauguraldissertation, Giesen, 2003, p. 166, line 15.
Pedersen et al., "Autoactivation of Human Recombinant Coagulation Factor VII", Biochemistry, vol. 28, pp. 9331-9336 (1989).
Petit et al., "GLP-1 receptor agonist In NAFLD", Diabetes & Metabolism, vol. 43, pp. 2S28-2S33 (2017).
Radaelli et al., "NAFLD/NASH in patients with type 2 diabetes and related treatment options", Journal of Endocrinological Investigation, vol. 41, pp. 509-521 (2018).
Salas et al., "Enhanced Pharmacokinetics of Factor VIIa as a Monomeric Fc Fusion", Thrombisis Research, vol. 135, pp. 970-976 (2015).
Skosyrev et al., "The Dependence of Stability of the Green Fluorescent Protein-Obelin Hybrids on the Nature of Their Constituent Modules and the Structure of the Amino Acid Linker", Russian Journal of Bioorganic Chemistry, vol. 27, No. 5, pp. 364-371, (2001).
Tang et al., "Selection of Linkers for a Catalytic Single-chain Antibody Using Phage Display Technology", The Journal of Biological Chemistry, vol. 271, No. 26, pp. 15682-15686 (1996).
Treetharnmathurot et al., "Effect of PEG molecular weight and linking chemistry on the biological activity and thermal stability of PEGylated trypsin", International Journal of Pharmaceutics, vol. 357, pp. 252-259 (2008).
Uchida et al., "Analysis of binding properties between 20 kDa human growth hormone (hGH) and hGH receptor (hGHR): the binding affinity for hGHR extracellular domain and mode of receptor dimerization", Journal of Molecular Endocrinology, vol. 23, pp. 347-353 (1999).
Weimer et al., "Prolonged in-vivo half-life of factor VIIa by fusion to albumin", Thromb Haemost, vol. 99, pp. 659-667 (2008).
Wen et al., "Discovery and Investigation of O-Xylosylation in Engineered Proteins Containing a (GGGGS) Linker", Analytical Chemistry, vol. 85, pp. 4805-4812, (2013).
Wu et al., "Separating mitogenic and metabolic activities of fibroblast growth factor 19 (FGF19)", PNAS, vol. 107, No. 32, pp. 14158-14163 (2010).

Xu et al., "Acute glucose-lowering and insulin-sensitizing action of FGF21 in insulin-resistant mouse models—association with liver and adipose tissue effects", Am J Physiol Endocrinol Metab, vol. 297, pp. E1105-E1114 (2009).
Xu et al., "Fibroblast Growth Factor 21 Reverse Hepatic Steatosis, Increases Energy Expenditure, and Improves Insulin Sensitivity in Diet-induced Obese Mice", Diabetes, vol. 58, pp. 250-259 (2009).
Yie et al., "FGF21 N- and C-termini play different roles in receptor interaction and activation", FEBS Letters, vol. 583, pp. 19-24 (2009).
International Preliminary Report on Patentability and Written Opinion for Application No. PCT/CN2016/106011 dated Feb. 19, 2019.
International Preliminary Report on Patentability and Written Opinion for Application No. PCT/CN2017/079871 dated Feb. 19, 2019.
Russian Office Action for Application No. 2019106765/10(013011) dated Dec. 25, 2019.
European Office Action for Application No. 16913393.1 dated Jun. 17, 2020.
Chinese Office Action for Application No. 201910687158.3 dated Jul. 1, 2020.
Russian Office Action for Application No. 2019135518/10(070134) dated Jul. 2, 2020.
Korean Office Action for Application No. 20197007918 dated Jul. 17, 2020.
Restriction Requirement for U.S. Appl. No. 16/326,412 dated Jan. 8, 2020.
Non-Final Office Action for U.S. Appl. No. 16/326,412 dated May 13, 2020.
Final Office Action for U.S. Appl. No. 16/326,412 dated Oct. 27, 2020.
Japanese Office Action for Application No. 2019-530527 dated Nov. 24, 2020.
Advisory Action for U.S. Appl. No. 16/326,412 dated Dec. 7, 2020.
Korean Office Action for Application No. 20197007918 dated Jan. 7, 2021.
Non-Final Office Action for U.S. Appl. No. 16/326,412 dated Feb. 16, 2021.
Notice of Allowance for U.S. Appl. No. 16/326,412 dated May 27, 2021.
Canadian Office Action for Application No. 3059662 dated Oct. 6, 2020.
Canadian Office Action for Application No. 3059994 dated Oct. 28, 2020.
Extended European Search Report for Application No. 17840761.5 dated Jan. 29, 2021.
Non-Final Office Action for U.S. Appl. No. 16/479,494 dated Sep. 27, 2021.
Canadian Office Action for Application No. 3059994 dated Sep. 1, 2021.
Canadian Office Action for Application No. 3059662 dated Sep. 1, 2021.

* cited by examiner

| | |
|---|---|
| 1 | ATGCAGCGCGTGAACATGATCATGGCAGAATCACCAGGCCTCATCACCATCTGCCTTTTA |
| 1 | M  Q  R  V  N  M  I  M  A  E  S  P  G  L  I  T  I  C  L  L |
| 61 | GGATATCTACTCAGTGCTGAATGTACAGTTTTTCTTGATCATGAAAACGCCAACAAAATT |
| 21 | G  Y  L  L  S  A  E  C  T  V  F  L  D  H  E  N  A  N  K  I |
| 121 | CTGAATCGGCCAAAGAGGTATAATTCAGGTAAATTGGAAGAGTTTGTTCAAGGGAATCTA |
| 41 | L  N  R  P  K  R  Y  N  S  G  K  L  E  E  F  V  Q  G  N  L |
| 181 | GAGAGAGAATGTATGGAAGAAAAGTGTAGTTTTGAAGAAGCACGAGAAGTTTTTGAAAAC |
| 61 | E  R  E  C  M  E  E  K  C  S  F  E  E  A  R  E  V  F  E  N |
| 241 | ACTGAAAGAACAACTGAATTTTGGAAGCAGTATGTTGATGGAGATCAGTGTGAGTCCAAT |
| 81 | T  E  R  T  T  E  F  W  K  Q  Y  V  D  G  D  Q  C  E  S  N |
| 301 | CCATGTTTAAATGGCGGCAGTTGCAAGGATGACATTAATTCCTATGAATGTTGGTGTCCC |
| 101 | P  C  L  N  G  G  S  C  K  D  D  I  N  S  Y  E  C  W  C  P |
| 361 | TTTGGATTTGAAGGAAAGAACTGTGAATTAGATGTAACATGTAACATTAAGAATGGCAGA |
| 121 | F  G  F  E  G  K  N  C  E  L  D  V  T  C  N  I  K  N  G  R |
| 421 | TGCGAGCAGTTTTGTAAAAATAGTGCTGATAACAAGGTGGTTTGCTCCTGTACTGAGGGA |
| 141 | C  E  Q  F  C  K  N  S  A  D  N  K  V  V  C  S  C  T  E  G |
| 481 | TATCGACTTGCAGAAAACCAGAAGTCCTGTGAACCAGCAGTGCCATTTCCATGTGGAAGA |
| 161 | Y  R  L  A  E  N  Q  K  S  C  E  P  A  V  P  F  P  C  G  R |
| 541 | GTTTCTGTTTCACAAACTTCTAAGCTCACCCGTGCTGAGACTGTTTTTCCTGATGTGGAC |
| 181 | V  S  V  S  Q  T  S  K  L  T  R  A  E  T  V  F  P  D  V  D |
| 601 | TATGTAAATTCTACTGAAGCTGAAACCATTTTGGATAACATCACTCAAAGCACCCAATCA |
| 201 | Y  V  N  S  T  E  A  E  T  I  L  D  N  I  T  Q  S  T  Q  S |
| 661 | TTTAATGACTTCACTCGGGTTGTTGGTGGAGAAGATGCCAAACCAGGTCAATTCCCTTGG |
| 221 | F  N  D  F  T  R  V  V  G  G  E  D  A  K  P  G  Q  F  P  W |
| 721 | CAGGTTGTTTTGAATGGTAAAGTTGATGCATTCTGTGGAGGCTCTATCGTTAATGAAAAA |
| 241 | Q  V  V  L  N  G  K  V  D  A  F  C  G  G  S  I  V  N  E  K |
| 781 | TGGATTGTAACTGCTGCCCACTGTGTTGAAACTGGTGTTAAAATTACAGTTGTCGCAGGT |
| 261 | W  I  V  T  A  A  H  C  V  E  T  G  V  K  I  T  V  V  A  G |
| 841 | GAACATAATATTGAGGAGACAGAACATACAGAGCAAAAGCGAAATGTGATTCGAATTATT |
| 281 | E  H  N  I  E  E  T  E  H  T  E  Q  K  R  N  V  I  R  I  I |
| 901 | CCTCACCACAACTACAATGCAGCTATTAATAAGTACAACCATGACATTGCCCTTCTGGAA |
| 301 | P  H  H  N  Y  N  A  A  I  N  K  Y  N  H  D  I  A  L  L  E |
| 961 | CTGGACGAACCCTTAGTGCTAAACAGCTACGTTACACCTATTTGCATTGCTGACAAGGAA |
| 321 | L  D  E  P  L  V  L  N  S  Y  V  T  P  I  C  I  A  D  K  E |
| 1021 | TACACGAACATCTTCCTCAAATTTGGATCTGGCTATGTAAGTGGCTGGGGAAGAGTCTTC |
| 341 | Y  T  N  I  F  L  K  F  G  S  G  Y  V  S  G  W  G  R  V  F |
| 1081 | CACAAAGGGAGATCAGCTTTAGTTCTTCAGTACCTTAGAGTTCCACTTGTTGACCGAGCC |
| 361 | H  K  G  R  S  A  L  V  L  Q  Y  L  R  V  P  L  V  D  R  A |
| 1141 | ACATGTCTTCGATCTACAAAGTTCACCATCTATAACAACATGTTCTGTGCTGGCTTCCAT |
| 381 | T  C  L  R  S  T  K  F  T  I  Y  N  N  M  F  C  A  G  F  H |
| 1201 | GAAGGAGGTAGAGATTCATGTCAAGGAGATAGTGGGGGACCCCATGTTACTGAAGTGGAA |

Figure 1

```
401        E  G  G  R  D  S  C  Q  G  D  S  G  G  P  H  V  T  E  V  E
1261    GGGACCAGTTTCTTAACTGGAATTATTAGCTGGGGTGAAGAGTGTGCAATGAAAGGCAAA
421        G  T  S  F  L  T  G  I  I  S  W  G  E  E  C  A  M  K  G  K
1321    TATGGAATATATACCAAGGTGTCCCGGTATGTCAACTGGATTAAGGAAAAAACAAAGCTC
441        Y  G  I  Y  T  K  V  S  R  Y  V  N  W  I  K  E  K  T  K  L
1381    ACTGGATCCGGTGGCGGTGGCTCCGGTGGAGGCGGAAGCGGCGGTGGAGGATCAGGCGGT
461        T  G  S  G  G  G  G  S  G  G  G  G  S  G  G  G  G  S  G  G
1441    GGAGGTAGCGGCGGAGGCGGTAGCTCCAGCTCTAGTAAAGCTCCCCCTCCTTCCCTGCCC
481        G  G  S  G  G  G  G  S  S  S  S  K  A  P  P  P  S  L  P
1501    TCACCCTCAAGACTGCCTGGACCTTCCGACACTCCCATCCTGCCACAGGTGGAGTGCCCT
501        S  P  S  R  L  P  G  P  S  D  T  P  I  L  P  Q  V  E  C  P
1561    CCATGTCCAGCACCCCCTGTCGCAGGTCCATCTGTGTTCCTGTTTCCACCCAAGCCTAAA
521        P  C  P  A  P  P  V  A  G  P  S  V  F  L  P  P  P  K  P  K
1621    GACCAGCTGATGATCTCCCGCACCCCAGAAGTCACCTGTGTGGTCGTGGATGTGAGCCAT
541        D  Q  L  M  I  S  R  T  P  E  V  T  C  V  V  V  D  V  S  H
1681    GAAGACCCCGAGGTCCAGTTCAATTGGTACGTGGATGGCGTCGAGGTGCACAACGCTAAG
561        E  D  P  E  V  Q  F  N  W  Y  V  D  G  V  E  V  H  N  A  K
1741    ACAAAACCTAGAGAAGAGCAGTTCAACTCTACCTTTCGCGTCGTGAGTGTGCTGACAGTC
581        T  K  P  R  E  E  Q  F  N  S  T  F  R  V  V  S  V  L  T  V
1801    GTGCACCAGGACTGGCTGAATGGCAAGGAGTATAAGTGCAAAGTGAGCAACAAAGGACTG
601        V  H  Q  D  W  L  N  G  K  E  Y  K  C  K  V  S  N  K  G  L
1861    CCTGCCTCAATCGAAAAGACTATTTCCAAGACCAAAGGACAGCCAAGAGAGCCCCAGGTG
621        P  A  S  I  E  K  T  I  S  K  T  K  G  Q  P  R  E  P  Q  V
1921    TACACCCTGCCTCCAAGCCGCGAAGAGATGACTAAAAATCAGGTCTCTCTGACCTGTCTG
641        Y  T  L  P  P  S  R  E  E  M  T  K  N  Q  V  S  L  T  C  L
1981    GTGAAGGGGTTTTATCCTAGTGATATCGCCGTGGAATGGGAGTCAAACGGTCAGCCAGAG
661        V  K  G  F  Y  P  S  D  I  A  V  E  W  E  S  N  G  Q  P  E
2041    AACAATTACAAGACCACACCCCCTATGCTGGACAGCGATGGGTCTTTCTTTCTGTATAGC
681        N  N  Y  K  T  T  P  P  M  L  D  S  D  G  S  F  F  L  Y  S
2101    AAACTGACAGTGGACAAGTCTCGGTGGCAGCAGGGTAACGTCTTCTCTTGCAGTGTGCTG
701        K  L  T  V  D  K  S  R  W  Q  Q  G  N  V  F  S  C  S  V  L
2161    CACGAAGCACTGCACAATCATTACACCCAGAAGTCACTGTCACTGAGCCCAGGAAAATGA
721        H  E  A  L  H  N  H  Y  T  Q  K  S  L  S  L  S  P  G  K
```

Figure 1 cont'd

HUMAN COAGULATION FACTOR IX (FIX) FUSION PROTEIN, PREPARATION METHOD THEREFOR, AND USE THEREOF

TECHNICAL FIELD

The present invention relates to the field of fusion proteins and, more specifically, to a fusion protein of human coagulation factor IX (FIX), preparation method and use thereof, especially the use for the treatment of various coagulation-related diseases.

BACKGROUND

Hemophilia B is an X-linked recessive inherited disease whose pathogenesis is a mutation in the human coagulation factor IX (FIX) gene located on the X chromosome, which results in a significant decrease in the content or activity of the coagulation factor in plasma, and thus impedes the intrinsic coagulation pathway and causes coagulation abnormalities. It is estimated that the total number of hemophilia B patients in China is about 20,000, accounting for 15%-20% of hemophilia. Hemophilia B affects one in 30000 males, while rarely occurs among females. The most common treatment currently used is FIX replacement therapy involving use of FIX enriched from plasma or expressed by recombinant cell.

Human coagulation factor IX (FIX) is a serine protease zymogen containing 461 amino acids and is an important component of the intrinsic coagulation cascade. It is mainly synthesized in the liver and secreted into the plasma. FIX consists of a number of separate functional domains, including a signal peptide, a propeptide region, a Gla domain, two epidermal growth factor (EGF) domains, an activating peptide, and a tryptase catalytic domain (serine protease domain). The zymogen is further processed into an active form by binding the light and heavy chains thereof via a disulfide bonds to form a heterodimer. FIX plays an important role in the intrinsic coagulation pathway. Only activated FIXa activates FX together with activated FVIII (FVIIIa), phospholipids and $Ca^{2+}$ into FXa to initiate a common coagulation pathway and exert a clotting effect. More than 100 mutations in FIX have been recorded in the current study. Some of them do not cause any clinical symptoms, but others lead to significant bleeding disorders. If left untreated, hemophilia B can cause uncontrollable bleeding in muscles, joints and body cavities after injury and may lead to death. In the past, this disease was mainly treated by administrating FIX prepared from human plasma. However, on one hand the treatment brings a consequent risk of contracting blood-borne viruses including human immunodeficiency virus (HIV) and hepatitis C virus (HCV). On the other hand, native FIX has a short half-life in humans, which is about 18 to 24 hours. Patients need repetitive transfusions of blood or blood products, which is not only expensive, but also may cause severe blood transfusion reactions. Trace amount of activated factors in the thrombin zymogen complex may also activate the coagulation cascade, causing thrombosis and embolism. At present, the half-life of commercially available recombinant FIX is relatively short, only 18 hours, such that hemophilia patients need to receive frequent intravenous administration in the emergency on-demand treatment after hemorrhage or in the prophylaxis before hemorrhage. Hemophilia B patients are recommended to receive an injection of FIX at a dose of 40~100 IU/kg 2 or 3 times a week to prevent bleeding events. Therefore, the development of long-acting recombinant FIX preparations with extended the half-life in plasma can not only reduce the number of administrations, but also reduce the physical and mental burden of patients, and greatly improve patient compliance.

To extend the in vivo functional half-life of FIX, half-life extending moieties such as PEG, human serum albumin (HSA), XTEN, CTP or IgG Fc have been linked to the FIX in the prior art. For example, N9-GP (PEGylated) from Novo Nordisk, FIX-FP (a HSA fusion protein) from CSL Behring and the long-acting FIX-CTP (a CTP fusion protein) from OPKO/Prolor have entered clinical trials. Clinical trials of N9-GP showed that the half-life of FIX was prolonged by 5 times (with an average half-life of 110 h) after a total of 3 administrations. However, one patient with severe hypersensitivity reaction and three patients with development of non-inhibitory antibodies were observed in the trial. The immunogenicity of N9-GP remains to be further studied (Collins P W et al, Blood, 2014, 124(26): 3880-3886). Clinical trials of FIX-FP showed that the half-life of FIX-FP was 89-96 hours, and no special immune response occurred in patients. Studies on FIX-CTP in a hemophilia B mouse model showed that the half-life of FIX was prolonged by 4 times and the bleeding frequency and duration was decreased, but the activity of FIX was also reduced (Hart Get. al., Haemophilia, 2012, 18: 32). The first fusion protein of FIX with Fc (FIX-Fc) was approved by the U.S. FDA in March 2014 under the trade name Alprolix (Biogen Idec) and is currently the only approved recombinant long-acting FIX drug. Alprolix is a fusion protein formed by covalently binding a single FIX molecule to the N-terminus of the double-stranded Fc fragment of human IgG1, and is recombinantly expressed by HEK-293H cells. Clinical studies have shown that Alprolix has a half-life of 57-86 hours, and the administration frequency thereof can be once every 7 or 10 days when used for prophylaxis. Currently, Alprolix has been approved for listing in several countries around the world. However, the fusion of Fc inevitably causes a decrease in specific activity. The in vitro activity determination confirmed that the molar specific activity of FIX-Fc (IU/nmol) was only 50% of that of FIX (BeneFIX®) (Peters R T et. al., Blood, 2010, 115(10):2057-64).

CTP is a short peptide derived from the carboxyl terminus of the human chorionic gonadotropin (hCG) beta subunit. It has been shown to have the ability to extend in vivo half-lives. Chinese Patent Nos. CN103539860A and CN103539861A disclosed a fusion protein in which CTP is used as a linker to link the β subunit and the a subunit of FSH to prolong the in vivo half-life of the fusion protein. Patent WO2013121416 disclosed a long-acting coagulation factor IX comprising at least one CTP linked to the carboxyl terminus of coagulation factor IX. The FIX-(CTP)$_3$, which contains three tandem CTPs, exhibits improved pharmacokinetic properties relative to rhFIX, FIX-CTP or FIX-CTP-CTP; FIX-CTP has a comparable in vitro activity and half-life to rhFIX; and the half-life of FIX-CTP-CTP is 3 times that of rhFIX, and the half-life of FIX-(CTP)$_3$ is 2.5-4 times that of rhFIX in rats and FIX-deficient mice. However, FIX-(CTP)$_3$ shows reduced clotting activity in the in vivo coagulation assay. In addition, compared with BeneFIX, the clotting activity of FIX-(CTP)$_3$ is delayed for 1 hour, which may because that the addition of three tandem CTPs may mask the activation site of FIX, thereby delaying the cascade.

The present inventors do not use CTP alone as a linker or as a half-life prolonging moiety as suggested by the prior art, but instead connect it to a flexible peptide linker (e.g., (GGGGS)n) (SEQ ID NO: 21) to form a hybrid linker peptide composed of a flexible peptide linker comprising GS and a rigid CTP peptide linker comprising a plurality of glycosyl side chains. The hybrid linker peptide linker is located between FIX and the half-life prolonging moiety (e.g., the immunoglobulin Fc fragment, which does not contain the CTP as suggested by the prior art) to constitute a new FIX fusion protein, not only further prolonging the half-life, but also reducing the immunogenicity, improving the bioavailability, greatly reducing the steric hindrance effect of the fusion ligand Fc on FIX, and maintaining good biological activity and function.

SUMMARY

The present invention provides a highly-glycosylated, homodimeric Fc fusion protein of coagulation factor IX (FIX). The fusion protein has a prolonged in vivo active half-life, low immunogenicity, and similar biological activity to a recombinant FIX. In addition, the present invention provides a method for efficiently and stably expressing the fusion protein. The fusion protein expressed by the method has advantages of high yield, good stability during preparation and storage, and similar biological activity to recombinant FIXs on the market.

In one aspect of the present invention, a highly-glycosylated FIX fusion protein is provided, which comprises, in order from the N-terminus to C-terminus, human coagulation factor IX (hFIX), a flexible peptide linker (Linker, L), at least one rigid unit comprising the carboxyl terminal peptide of human chorionic gonadotropin β subunit (CTP) and a half-life extending moiety (such as an immunoglobulin Fc fragment, an albumin, a transferrin or PEG, preferably a human IgG Fc variant (indicated as vFc)). In some preferred embodiments of the present invention, the fusion protein is indicated as hFIX-L-CTP-vFc.

The hFIX is a wild-type hFIX or a mutant thereof. Further, the wild type hFIX has the amino acid sequence as shown in SEQ ID NO: 1. Preferably, the hFIX mutant is at least 85% homologous to the amino acid sequence as shown in SEQ ID NO: 1. More preferably, the hFIX mutant is at least 90% homologous to the amino acid sequence as shown in SEQ ID NO: 1. Most preferably, the hFIX mutant is at least 95% homologous to the amino acid sequence as shown in SEQ ID NO: 1.

The flexible peptide linker is preferably non-immunogenic and can generate sufficient spatial distance between hFIX and Fc to minimize the steric effects between each other. Preferably, a flexible peptide linker consisting of two or more amino acid residues selected from the group consisting of Gly (G), Ser (S), Ala (A) and Thr (T) is used. Preferably, the flexible peptide linker comprises residues G and S. The length of the linker peptide plays a very important role in the activity of the fusion protein. For the purposes of the present invention, the peptide linker may preferably comprise a general formula of the amino acid sequence formed by combining repetitive units (GS)a(GGS)b(GGGS)c(GGGGS)d (SEQ ID NO: 20), wherein each a, b, c, and d is an integer equal to or greater than 0, and a+b+c+d≥1.

Specifically, in some embodiments of the present invention, the peptide linker may preferably comprise the following sequences:

```
(i) L1:                   (SEQ ID NO: 10)
GSGGGSGGGGSGGGGS;

(ii) L2:                  (SEQ ID NO: 11)
GSGGGGSGGGGSGGGGSGGGGSGGGGS;

(iii) L3:                 (SEQ ID NO: 12)
GGGGSGGGGSGGGGSGGGGS;

(iv) L4:                  (SEQ ID NO: 13)
GSGGGGSGGGGSGGGGSGGGGSGGGGSGGGGSGGGGS;

(v) L5:                   (SEQ ID NO: 14)
GGGSGGGSGGGSGGGSGGGS;
```

The CTP rigid unit is selected from a full-length sequence consisting of carboxyl-terminal amino acids 113 to 145 of human chorionic gonadotropin β subunit, or a fragment thereof. Specifically, the CTP rigid unit comprises the amino acid sequence as shown in SEQ ID NO: 2 or a truncated sequence thereof. First, the CTP peptide which occurs naturally in the human body is non-immunogenic. Second, compared to the random coil of a flexible peptide linker, the rigid CTP peptide linker containing multiple glycosylation sites can form a stable steric conformation, which facilitates FIX and the Fc segment to fold independently into correct three-dimensional conformations without affecting the individual biological activities of each other. Moreover, the glycosyl side chains of CTP have a protective effect that can reduce the sensitivity of the peptide linker to proteases.

Preferably, the CTP rigid unit contains at least 2 glycosylation sites. For example, in a preferred embodiment of the present invention, the CTP rigid unit contains 2 glycosylation sites. Illustratively, the CTP rigid unit contains N-terminal 10 amino acids of SEQ ID NO: 2, i.e. SSSS*KAPPPS* (SEQ ID NO: 15); alternatively, the CTP rigid unit contains C-terminal 14 amino acids of SEQ ID NO: 2, i.e. S*RLPGPS*DTPILPQ. As another example, in another embodiment, the CTP rigid unit contains 3 glycosylation sites. Illustratively, the CTP rigid unit contains N-terminal 16 amino acids of SEQ ID NO: 2, i.e. SSSS*KAPPPS*LPSPS*R (SEQ ID NO: 17). As another example, in other embodiments, the CTP rigid unit contains 4 glycosylation sites. Illustratively, the CTP rigid unit contains 28, 29, 30, 31, 32, or 33 amino acids, starting from position 113, 114, 115, 116, 117, or 118 and ending at position 145 of the human chorionic gonadotropin beta subunit. Specifically, the CTP rigid unit contains N-terminal 28 amino acids of SEQ ID NO: 2, i.e. SSSS*KAPPPS*LPSPS*RLPGPS*DTPILPQ (SEQ ID NO: 18). Herein, * represents a glycosylation site. Each possibility represents a separate embodiment of the present invention.

In other embodiments, the CTP rigid unit provided by the present invention is at least 70% homologous to the amino acid sequence of native CTP. In other embodiments, the CTP rigid unit provided by the present invention is at least 80% homologous to the amino acid sequence of native CTP. In other embodiments, the CTP rigid unit provided by the present invention is at least 90% homologous to the amino acid sequence of native CTP. In other embodiments, the CTP rigid unit provided by the present invention is at least 95% homologous to the amino acid sequence of native CTP.

In specific embodiments of the present invention, the CTP rigid unit may preferably comprise the following sequences:

```
(i) CTP¹:              (SEQ ID NO: 2)
PRFQDSSSSKAPPPSLPSPSRLPGPSDTPILPQ;

(ii) CTP²:             (SEQ ID NO: 18)
SSSSKAPPPSLPSPSRLPGPSDTPILPQ;

(iii) CTP³:            (SEQ ID NO: 15)
SSSSKAPPPS;

(iv) CTP⁴:             (SEQ ID NO: 16)
SRLPGPSDTPILPQ.
```

In some embodiments of the present invention, the fusion protein comprises one CTP rigid unit as described above. In other embodiments of the present invention, the fusion protein may comprise 2 or more, preferably 2, 3, 4 or 5, CTP rigid units as described above. For example, in an embodiment of the present invention, the fusion protein comprises 2 CTP³ rigid units: SSSSKAPPPSSSSSKAPPPS (SEQ ID NO: 19) (CTP³-CTP³, or expressed as (CTP³) 2).

The half-life extending moiety is preferably selected from the group consisting of Fc fragments of immunoglobulin IgG, IgM, and IgA, more preferably from the group consisting of Fc fragments of human IgG1, IgG2, IgG3 and IgG4 and variants thereof. Further, the human IgG Fc variant comprises at least one amino acid modification in the wild-type human IgG Fc and has reduced effector function (ADCC and/or CDC effects) and/or enhanced binding affinity to the neonatal Fc receptor (FcRn). Further, the human IgG Fc variant may be selected from the group consisting of:
  (i) vFcγ1: hinge, CH2 and CH3 regions of human IgG1 with mutations Leu234Val, Leu235Ala, and Pro331Ser (the amino acid sequence as shown in SEQ ID NO: 3);
  (ii) vFcγ2-1: hinge, CH2 and CH3 regions of human IgG2 with mutation Pro331Ser (the amino acid sequence as shown in SEQ ID NO: 4);
  (iii) vFcγ2-2: hinge, CH2 and CH3 regions of human IgG2 with mutations Thr250Gln and Met428Leu (the amino acid sequence as shown in SEQ ID NO: 5);
  (iv) vFcγ2-3: hinge, CH2 and CH3 regions of human IgG2 with mutations Pro331Ser, Thr250Gln and Met428Leu (the amino acid sequence as shown in SEQ ID NO: 6).
  (iv) vFcγ4: hinge, CH2 and CH3 regions of human IgG4 with mutations Ser228Pro and Leu235Ala (the amino acid sequence as shown in SEQ ID NO: 7).

The Fc variant (vFc) in the fusion protein of the present invention comprises hinge, CH2 and CH3 regions of human IgG such as human IgG1, IgG2 and IgG4. The CH2 region contains amino acid mutations at positions 228, 234, 235 and 331 (as defined by the EU numbering system). It is believed that these amino acid mutations reduce the effector functions of Fc. Human IgG2 Fc does not bind to FcγR but shows extremely weak complement activity. An Fcγ2 variant with mutation Pro331Ser should have less complement activity than native Fcγ2 while remain as a non-binder to FcγR. IgG4 Fc is deficient in activating the complement cascade, and its binding affinity to FcγR is about an order of magnitude lower than that of IgG1. An Fcγ4 variant with mutation Leu235Ala should exhibit minimal effector functions as compared to the native Fcγ4. An Fcγ1 variant with mutations Leu234Val, Leu235Ala and Pro331Ser also should exhibit decreased effector functions than the native Fcγ1. These Fc variants are more suitable for the preparation of FIX fusion proteins than native human IgG Fcs. The amino acid mutations at positions 250 and 428, as defined by the EU numbering system, increase the binding affinity of the Fc region to the neonatal receptor FcRn, thereby further prolonging the half-life (Paul R et al., J Biol Chem, 2004, 279:6213-6216). The above two types of functional variants are combined or added on each other to generate new combination variants to reduce the effector functions while prolonging the half-life. The Fc variants of the present invention contain mutations at, but not limited to, the above-described sites. Substitutions may be introduced at other sites such that Fcs have reduced effector functions and/or enhanced binding affinity to FcRn. Such substitutions should not lead to a decrease in the function/activity or undesirable conformational changes of the Fc variants. Common mutation sites may be found in Shields R L et al., J Biol Chem, 2001,276(9):6591-604.

In a preferred embodiment of the present invention, the fusion protein has the amino acid sequence as shown in SEQ ID NO: 8.

According to another aspect of the present invention, a DNA encoding the fusion protein described above is provided.

In a preferred embodiment of the present invention, the fusion protein has the DNA sequence as shown in SEQ ID NO: 9.

According to another aspect of the present invention, a vector which comprises the DNA described above is provided.

According to another aspect of the present invention, a host cell which comprises or is transfected with the vector described above is provided.

In a specific embodiment of the present invention, the host cell is CHO-derived cell line DXB-11.

According to the fifth aspect of the present invention, a pharmaceutical composition is provided. The pharmaceutical composition comprises a pharmaceutically acceptable carrier, excipient or diluent, and an effective amount of the fusion protein described above.

According to another aspect of the present invention, a method of preparing or producing the fusion protein from a mammalian cell line, such as a CHO-derived cell line, is provided, which comprises the steps of:
  (a) introducing a DNA encoding the fusion protein described above into a CHO cell to generate a CHO-derived cell line;
  (b) screening the high-yielding cell line in step (a) which expresses more than 1 mg/10⁶ cells per 24 hours in its growth medium;
  (c) growing the cell line obtained in step (b) to express the fusion protein;
  (d) harvesting the fermentation broth obtained in step (c) and isolating and purifying the fusion protein.

Further, the CHO-derived cell line in step (a) is DXB-11.

Further, the cell culture in step (c) may be carried out by using a batch, perfusion or fed-batch culture method.

Further, in step (d), the fusion protein is purified by a four-step chromatography procedure, i.e., affinity chromatography, hydrophobic chromatography, anion exchange chromatography, and molecular sieve chromatography. The present invention further gives preferred purification conditions in Example 5.

In a preferred embodiment of the present invention, the fusion protein prepared by the above method has an activity of >200 IU/mg.

According to a sixth aspect of the present invention, there is provided use of the fusion protein in the manufacture of a medicament for the prevention or treatment of a hemorrhagic disease or event resulting from a deficiency or functional defect of FIX, comprising use in the manufacture of a medicament for the prevention or treatment of a hemorrhagic disease in a patient with congenital or acquired FIX deficiency, and use in the manufacture of a medicament for the prevention or treatment of spontaneous or surgical bleeding in a patient with hemophilia B.

The present inventors have found that the fusion proteins and their preparation methods as described and/or disclosed in the present invention have the following advantages:

1. The human IgG Fc variant which is used in the fusion protein as a fusion ligand is non-lytic and reduces the effector function triggered by binding to FcγRs and C1q.

2. Compared to recombinant FIXs, the fusion protein of the present invention can be expected to have reduced immunogenicity, which results in decreased production of neutralizing antibodies in patients.

3. The fusion protein of the present invention has good stability during fermentation, purification and storage.

4. The fusion protein provided by the present invention contains a rigid CTP peptide containing multiple glycosyl side chains. The rigid CTP peptide can form a stable steric conformation compared to the random coil of flexible linkers such as (GGGGS)n (SEQ ID NO: 21). This "block" effect causes the FIX and Fc fragment to fold independently into correct three-dimensional conformations without affecting the biological activities of each other. The highly sialylated, negatively charged CTP which contain glycosyl groups can resist the clearance by the kidney, thereby prolonging the half-life of the fusion protein. Moreover, the protective effect of the glycosyl side chains of CTP reduces the sensitivity of the peptide linker to proteases, such that the fusion protein is less susceptible to degradation in the linking region.

5. The preparation method of the fusion protein provided by the present invention is high-yield. After culturing in a 300 ml shake flask for 14 days, the cumulative yield can reach at least 200 mg/L. The method can be scaled up for large-scale industrial production.

6. Compared with the monomer-dimer heterozygous (Monomeric) FIX fusion protein constructed by Biogen, the expression and purification of the fusion protein constructed by the present invention are more efficient and convenient, significantly reducing the production cost. Biogen constructed a binary expression vector of rFIXFc and Fc, wherein the Fc molecular was labeled with Flag (EP Patent Publication No. EP1624891B1). The fermentation broth of the expressed fusion protein was expected to contain three forms of products, a homodimeric (Dimeric) fusion protein (FIX-Fc:FIX-Fc), a monomer-dimer heterozygous (Monomeric) fusion protein (FIX-Fc:FLAG-Fc), and a dimer (FLAG-Fc:FLAG-Fc). On one hand, during expression of the fusion protein, since the host cells need to simultaneously express single chain molecules of both FIX-Fc and Fc, and then the molecules should bind to each other to form the three products as described above, such that the final expression efficiency of the target product is greatly reduced. In addition, during the purification, side impurities in the other two forms have to be removed, which makes the purification more complex and makes the production efficiency low, and greatly increases the production cost. Compared to the Monomeric rFIXFc fusion protein developed by Biogen, the preparation method of the present invention has certain technical and price advantages. The expression and purification of the present invention are simpler and more efficient and the production cost is lower.

BRIEF DESCRIPTION OF DRAWINGS

FIG. 1 shows the nucleotide sequence (SEQ ID NO: 9) and deduced amino acid sequence (SEQ ID NO: 8) of the fusion protein inserted into the Spe I-EcoR I fragment in expression vector pF9-5B. The mature fusion protein contains hFIX, a flexible peptide linker (underlined with __), a CTP rigid unit (underlined with __) and a vFcγ$_{2-3}$ variant.

REFERENCE TO SEQUENCE LISTING

Figure 2:
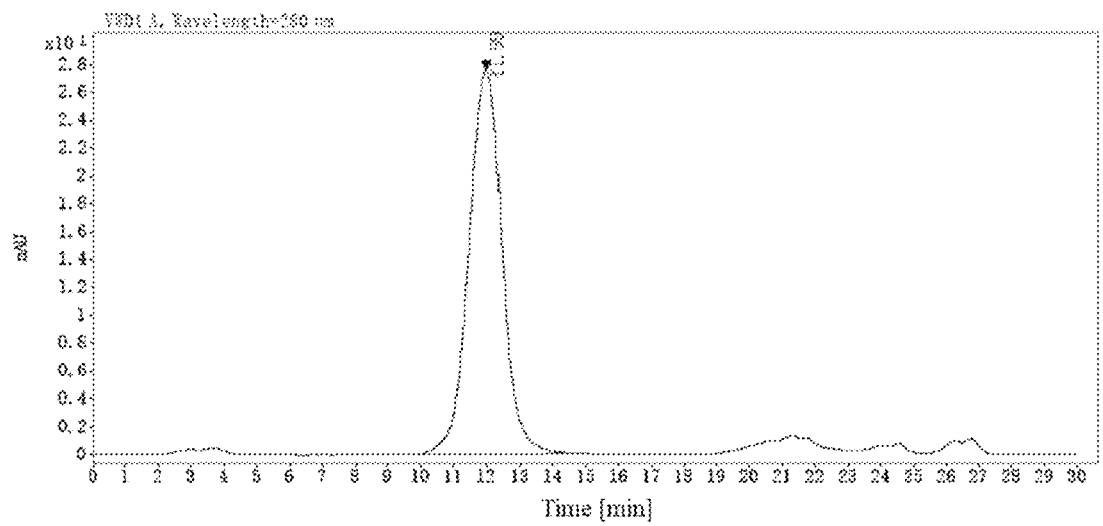
FIG. 2 shows the SEC-HPLC chromatogram of purified fusion protein F9-5B.

The Sequence Listing associated with the instant disclosure has been submitted electronically herewith as an 27 kilobyte file with File Name (Substitute Sequence Listing.txt), Creation Date (Aug. 17, 2021), Computer System (IBM-PC/MS-DOS/MS-Windows). The Sequence Listing submitted electronically herewith is hereby incorporated by reference into the instant disclosure.

DETAILED DESCRIPTION hCG-β Carboxyl Terminal Peptide (CTP)

CTP is a short peptide from the carboxyl terminus of the human chorionic gonadotropin (hCG) beta subunit. Four kinds of reproduction-related polypeptide hormones, follicle stimulating hormone (FSH), luteinizing hormone (LH), thyroid stimulating hormone (TSH), and human chorionic gonadotropin (hCG) contain the same alpha subunit and their respective specific beta subunits. Compared with the other three hormones, hCG has a significantly prolonged in vivo half-life, which is mainly due to the specific carboxyl terminal peptide (CTP) on the hCG β-subunit (Fares F A et al., Proc Natl Acad Sci USA, 1992, 89(10): 4304-4308). The native CTP contains 37 amino acid residues, including four O-glycosylation sites, and sialic acid residues at the terminus. The highly sialylated, negatively charged CTP can resist the clearance by the kidney, thereby prolonging the in vivo half-life of the protein (Fares F A et. al., Proc Natl Acad Sci USA, 1992, 89(10): 4304-4308). The present inventors creatively connect at least one CTP peptide with a flexible peptide linker having an appropriate length to form a new peptide linker, for linking FIX to a half-life extending moiety e.g., an immunoglobulin Fc fragment.

The present inventors have found that the addition of a CTP peptide between FIX and an Fc variant is equivalent to the addition of a rigid peptide linker. On one hand, the addition of the CTP peptide ensures that the N-terminally fused FIX does not affect the binding site in Fc variant for FcRn, thus having no effect on the half-life. In addition, the protein A binding site in Fc is important for purification steps. The addition of CTP ensures that the N-terminally fused FIX will not "cover" its binding site for protein A. Thus the fusion protein can be purified with a cheaper and more suitable filler, which reduces the cost of purification. On the other hand, the addition of a CTP rigid unit prevents the Fc fragment having a size of about 25 kD from interfering with the correct folding of the N-terminally fused FIX, thus leading to no loss or decline of the biological activity/function of the FIX. The rigid CTP peptide containing multiple glycosyl side chains can form a stable steric conformation compared to the random coil of flexible linkers such as (GGGGS)n (SEQ ID NO: 21). This "block" effect causes the FIX and Fc fragment to fold independently into correct three-dimensional conformations without affecting the biological activities of each other. Moreover, the protective effect of the glycosyl side chains of CTP reduces the sensitivity of the peptide linker to proteases, such that the fusion protein is less susceptible to degradation in the linking region.

IgG Fc Variants

Non-Lytic Fc Variants

The Fc element is derived from the constant region (Fc fragment) of immunoglobulin IgG, and plays an important role in eradicating pathogens in immune defense. The Fc-mediated effector functions of IgG function through two mechanisms as follows. (1) After binding to Fc receptors (FcγRs) on the cell surface, pathogens are broken down by phagocytosis or lysis or by killer cells through the antibody-dependent cell-mediated cytotoxicity (ADCC) pathway. (2) Alternatively, after binding to C1q of the first complement component C1, the complement-dependent cytotoxicity (CDC) pathway is triggered and thus pathogen are lysed. Among the four subtypes of human IgG, $IgG_1$ and $IgG_3$ are able to bind to FcγRs effectively, and $IgG_4$ has lower binding affinity for FcγRs. The binding of $IgG_2$ to FcγRs is too low to be measured, so human $IgG_2$ has little ADCC effects. In addition, human $IgG_1$ and $IgG_3$ can also effectively bind to C1q to activate the complement cascade. Human $IgG_2$ binds weakly to C1q and $IgG_4$ does not bind to C1q (Jefferis R et al., Immunol Rev, 1998, 163: 59-76), so the CDC effect of human $IgG_2$ is also weak. Obviously, none of the native IgG subtypes is well suited for constructing FIX-Fc fusion proteins. In order to obtain non-lytic Fc variants without effector functions, the most effective method is to mutate the complement- and receptor-binding regions of the Fc segment and adjust the binding affinity of Fc for related receptors to reduce or eliminate ADCC and CDC effects but retain only the biological activity of the functional protein and the long in vivo half-life of the Fc segment without the generation of cytotoxicity. More mutation sites contained in non-lytic Fc variants can be found in Shields R L et al., J Biol Chem, 2001,276(9):6591-604 or China Patent No. CN 201280031137.2.

Fc Variants with Enhanced Affinity to the Neonatal Receptor FcRn

The plasma half-life of IgG depends on its binding to FcRn. Typically, IgG binds to FcRn at pH 6.0 and dissociates from FcRn at pH 7.4 (plasma pH). Through the study on the binding sites of the two, the sites on IgG that bind to FcRn are modified to increase the binding affinity at pH 6.0. It has been proven that mutations of some residues in the human Fcγ domain, which are important for the binding to FcRn, can increase the serum half-life. Mutations in residues T250, M252, S254, T256, V308, E380, M428 and N434 have been reported to increase or decrease the FcRn-binding affinity (Roopenian et al., Nat. Review Immunology 7:715-725, 2007). Trastuzumab (Herceptin, Genentech) variants, disclosed in Korean Patent No. KR 10-1027427, show increased FcRn-binding affinity, and these variants contain one or more amino acid modifications selected from the group consisting of 257C, 257M, 257L, 257N, 257Y, 279Q, 279Y, 308F and 308Y. Bevacizumab (Avastin, Genentech) variants, provided in Korean Patent No. KR 2010-0099179, show prolonged in vivo half-life and these variants contain amino acid modifications N434S, M252Y/M428L, M252Y/N434S and M428L/N434S. In addition, Hinton et al. also found that two variants T250Q and M428L increased the binding affinity for FcRn by 3 and 7 times, respectively. When the two sites were mutated simultaneously, the binding affinity was increased by 28 times. In rhesus macaque, the M428L or T250Q/M428L variant shows a 2-fold increase in plasma half-life (Paul R. Hinton et al., J Immunol, 2006, 176:346-356). More mutation sites contained in Fc variants with increased binding affinity for FcRn can be found in China Patent No. CN201280066663.2. In addition, studies show that the T250Q/M428L mutations in the Fc regions of five humanized antibodies improve the interaction between the Fc domain and FcRn. Moreover, in subsequent in vivo pharmacokinetic tests, compared to wild-type antibodies, the Fc mutated antibodies show improved pharmacokinetic parameters, such as increased in vivo exposure, reduced clearance, and increased subcutaneous bioavailability, when administered via subcutaneous injection (Datta-Mannan A et al., MAbs. Taylor & Francis, 2012, 4(2):267-273.).

Fusion Protein and Preparation Method Thereof

The fusion protein gene of the present invention is artificially synthesized after codon optimization. Based on the nucleotide sequence of the present invention, one skilled in the art can conveniently prepare the nucleic acid of the present invention by various known methods, for example, but not limited to, artificial synthesis or traditional subcloning. For specific methods, see J. Sambrook, Molecular Cloning: A Laboratory Manual. As an embodiment of the present invention, the nucleic acid sequence of the present invention can be constructed by segmentally synthesizing nucleotide sequences followed by subcloning.

The present invention also provides an expression vector for mammalian cells comprising a sequence encoding a fusion protein of the present invention and an expression regulatory sequence operably linked thereto. By "operably link" or "operably linked to" is meant a condition in which some portions of a linear DNA sequence are capable of regulating or controlling the activity of other portions of the same linear DNA sequence. For instance, a promoter is operably linked to a coding sequence if the promoter controls the transcription of the sequence.

The expression vector for mammalian cells may be a commercially available vector such as, but not limited to, pcDNA3, pIRES, pDR, pBK, pSPORT and the like which can be used in a eukaryotic cell expression system. One skilled in the art can select a suitable expression vector based on the host cell.

The coding sequence of the fusion protein of the present invention may be introduced into suitable restriction sites by one skilled in the art by restriction enzyme cleavage and splicing according to a conventional method based on the restriction enzyme map of the known empty expression vector, to produce the recombinant expression vector of the present invention.

The present invention also provides a host cell expressing a fusion protein of the present invention comprising a coding sequence of a fusion protein of the present invention. The host cell is preferably a eukaryotic cell such as, but not limited to, CHO cells, COS cells, 293 cells, RSF cells and the like. In a preferred embodiment of the present invention, the cell is a CHO cell which can better express the fusion protein of the present invention to obtain a fusion protein having good activity and good stability.

The present invention also provides a method for producing a fusion protein of the present invention by using recombinant DNA technology, including the steps of:

1) providing a nucleic acid sequence encoding a fusion protein;

2) inserting the nucleic acid sequence of 1) into a suitable expression vector to obtain a recombinant expression vector;

3) introducing the recombinant expression vector of 2) into a suitable host cell; 4) growing the transfected host cell under conditions suitable for expression;

5) collecting the supernatant and purifying the fusion protein product.

The coding sequence can be introduced into a host cell by various techniques known in the art such as, but not limited to, calcium phosphate precipitation, lipofection, electroporation, microinjection, viral infection and method using alkali metal ions.

For the culture and expression of host cells, see Olander R M et. al., Dev Biol Stand, 1996, 86:338. The cells and debris in the suspension can be removed by centrifugation and the supernatant is collected.

The fusion protein obtained as described above can be purified to a substantially uniform nature, for example, showing a single band or specific bands on SDS-PAGE electrophoresis. The supernatant is firstly to be concentrated. The concentrated supernatant may be further purified by gel chromatography or by ion exchange chromatography, such as anion exchange chromatography or cation exchange chromatography. The gel matrix may be a matrix commonly used for protein purification such as agarose, dextran, polyamide, and the like. The Q- or SP-group is a preferred ion exchange group. Finally, the purified product may be further finely purified by methods such as hydroxyapatite adsorption chromatography, metal chelate chromatography, hydrophobic interaction chromatography and reversed-phase high performance liquid chromatography, and the like. All of the above purification steps can be used in different combinations to ultimately obtain proteins with a substantially uniform purity. The expressed fusion protein can be purified by using an affinity chromatography column containing an antibody, receptor or ligand specific for the fusion protein. Depending on the nature of the affinity column used, the fusion polypeptide bound to the affinity column can be eluted by using conventional methods such as high salt buffer, pH change, and the like.

Pharmaceutical Composition

The present invention also provides a pharmaceutical composition comprising an effective dose of a fusion protein of the present invention and a pharmaceutically acceptable carrier. In general, an effective amount of the fusion protein of the present invention may be formulated in a non-toxic, inert and pharmaceutically acceptable aqueous carrier medium, wherein the pH is generally about 5-8, preferably about 6-8. The term "effective amount" or "effective dose" refers to an amount that yields functional or active effects on humans and/or animals and is acceptable by humans and/or animals. "Pharmaceutically acceptable" ingredients are those that are suitable for use in humans and/or mammals without excessive adverse side effects (e.g., toxicity, irritation and allergies), i.e., substances with a reasonable benefit/risk ratio. The term "pharmaceutically acceptable carrier" refers to a carrier for delivering a therapeutic agent, and the carrier includes various excipients and diluents.

Pharmaceutically acceptable carriers include, but are not limited to, saline, buffer, glucose, water, glycerol, ethanol, and combinations thereof. In general, the pharmaceutical formulation should be compatible with the mode of administration. The pharmaceutical compositions of the present invention may be prepared in the form of injections, for example, prepared by conventional methods using physiological saline or aqueous solutions containing glucose and other adjuvants. The pharmaceutical compositions described above are preferably manufactured under aseptic conditions. The amount of the active ingredient administered is the therapeutically effective amount. The pharmaceutical formulation of the present invention can also be prepared in a sustained release form.

The effective amount of the fusion protein of the present invention may vary depending on the mode of administration and the severity of the disease to be treated. A preferred effective amount may be determined by one of ordinary skill in the art based on various factors for example by clinical trials. The factors include, but are not limited to, the pharmacokinetic parameters of the fusion protein such as bioavailability, metabolism, half-life, etc., the severity of the disease to be treated in a patient, the patient's weight, the patient's immune status, the route of administration, etc.

EXAMPLES

Example 1. Construction of an Expression Plasmid Encoding the FIX Fusion Protein The gene sequence encoding the full-length FIX and gene sequences encoding flexible peptide linkers with different lengths, CTP rigid peptides with different lengths and different IgG Fc variants were artificially-optimized, CHO cell-biased codons and can be obtained by chemical synthesis. A restriction site, SpeI or EcoRI respectively, were present at each of the 5'-end and 3'-end of the synthesized fragment to facilitate insertion of the target fragment into a specific site of the expression vector. The verified fusion gene was digested with SpeI and EcoRI, and then inserted between corresponding restriction sites in expression plasmid PXY1A1, which was obtained by modifying PCDNA3.1 as a template, to obtain an expression plasmid pF9-5 of the fusion gene. The plasmid PXY1A1 contains, but not limited to, the following important expression elements: 1) a human cytomegalovirus early promoter and an enhancer required for high exogenous expression in mammalian cells; 2) a double selection marker which may confer kanamycin resistance to bacteria and G418 resistance to mammalian cells; 3) an expression cassette of mouse dihydrofolate reductase (DHFR) gene, which allows the fusion gene and DHFR gene to be co-amplified in the presence of methotrexate (MTX) in DHFR gene-deficient host cells (See U.S. Pat. No. 4,399,216). The expression plasmid of the fusion protein was then transfected into a mammalian host cell line. DHFR enzyme-deficient CHO cells are preferred host cell line for stable expression at high levels (See U.S. Pat. No. 4,818,679).

As shown in Table 1, the present invention constructed a series of hFIX fusion proteins comprising flexible peptide linkers of different lengths, CTP rigid units of different compositions, and several different subtypes of IgG Fc (vFc) variant elements. The nucleotide sequence of F9-5B and the translated amino acid sequence thereof are shown in FIG. 1.

TABLE 1

Composition of several FIX fusion proteins constructed

| Name | Elemental composition of the fusion protein (from N-terminus to C-terminus) |
|---|---|
| F9-5A | FIX-L3-CTP$^1$-vFc$\gamma_1$ |
| F9-5B | FIX-L2-CTP$^2$-vFc$\gamma_{2-3}$ |

TABLE 1-continued

Composition of several FIX fusion proteins constructed

| Name | Elemental composition of the fusion protein (from N-terminus to C-terminus) |
|---|---|
| F9-5C | FIX-L5-CTP$^4$-vFc$\gamma_4$ |
| F9-5D | FIX-L1-CTP$^3$-CTP$^3$-vFc$\gamma_{2-2}$ |
| F9-5E | FIX-L4-CTP$^3$-vFc$\gamma_{2-1}$ |
| F9-5F | FIX-L2-vFc$\gamma_{2-3}$-CTP$^2$ |
| F9-5G | FIX-L4-vFc$\gamma_{2-3}$ |

Example 2. Transient Expression of Various Fusion Proteins and Determination of in Vitro Activity of the Same The series of expression plasmids as obtained in Example 1 were respectively transfected into 3×10$^7$ CHO-K1 cells in a 30 mL shake flask by using DNAFect LT Reagent™ (ATGCell), and the transfected cells were cultured in serum-free growth medium containing 1000 ng/mL of vitamin K1 for 5 days. The concentration of the fusion protein in the supernatant was measured and the activity thereof was determined by the method as described in Example 6. The ELISA results showed that the transient expression levels of these plasmids were similar under these conditions, but the coagulation activities of these fusion proteins showed large differences. The activities of F9-5B, F9-5C, F9-5D and F9-5E were 119.5%, 104.2%, 83.9% and 94.7%, respectively, of that of F9-5A, whose molar specific activity was defined as 100%. The activity of F9-5F was only about 30% of that of F9-5B, probably because that the CTP rigid unit which was placed at the N-terminus of Fc formed a fixed spatial conformation to effectively separate different functional regions of the fusion protein, which facilitated FIX and the Fc part to fold independently into correct three-dimensional conformations, thereby maintaining a high activity. The fusion protein in the supernatant of F9-5G cell culture mostly existed in the form of inactive polymers. This may be because that an over-length peptide linker can not increase the activity of the fusion protein, but instead will cause the protein to fold incorrectly and exist as inactive polymers.

Example 3 Expression of Fusion Proteins in Transfected Cell Lines

The expression plasm ids of the fusion proteins as described above were transfected into mammalian host cell lines to express FIX fusion proteins. DHFR-deficient CHO cells are preferred host cell line for stable expression at high levels (See U.S. Pat. No. 4,818,679). A preferred method of transfection was electroporation, and other methods including calcium phosphate co-deposition, liposome transfection and microinjection might also be used. In electroporation, Gene Pulser Electroporator (Bio-Rad Laboratories) was used at a voltage of 300 V and a capacitance of 1050 μFd, and 50 μg of Pvul-linearized expression plasmid was added to 3×10$^7$ cells placed in the cuvette. The electroporated cells were transferred to a shake flask containing 30 ml of growth medium. Two days after the transfection, the medium was replaced with a growth medium containing 0.6 mg/mL of G418. The cells were seeded in 96-well plates at a certain concentration and cultured for 12-15 days until large discrete cell clones appeared. Transfectants resistant to the selected drug were screened by an ELISA assay against human IgG Fc. Quantification of the expression of the fusion protein can also be performed by using an ELISA assay against FIX. The wells producing high levels of Fc fusion protein were subcloned by limiting dilutions.

To achieve higher levels of fusion protein expression, co-amplification utilizing the DHFR gene that can be inhibited by an MTX drug is preferred. The transfected gene of the fusion protein was co-amplified with the DHFR gene in growth media containing increasing concentrations of MTX. Subclones with positive DHFR expression were subjected to limiting dilution, and transfectants capable of growing in media containing up to 6 μM of MTX were screened by increasing the selection pressure gradually. The transfectants were measured for secretion rates and cell lines yielding high levels of exogenous protein were screened. Cell lines with a secretion rate of more than about 1, preferably about 2 mg/10$^6$ [i.e. million] cells/24 h, were adapted to suspension culture by using serum-free growth media. Conditioned media was then used to purify the fusion protein.

Example 4. Production of Fusion Proteins

First, the high-yielding cell lines obtained in Example 3 were subjected to serum-free adaptation culturing in a petri dish and then transferred to a shake flask for suspension adaptation culturing. After these cells were adapted to these culture conditions, they were fed-batch cultured in a 300 mL shake flask, or a perfusion culture was simulated by replacing the medium daily. The CHO-derived cell line expressing the fusion protein F9-5B obtained in Example 3 was fed-batch cultured in a 300 mL shake flask for 14 days. The cumulative yield of the expressed recombinant fusion protein reached 200 mg/L, and the viable cell density reached up to 18×10$^6$ cells/m L. 1000 mL shake flasks could be used for producing more fusion proteins. In another culture method, the CHO-derived cell line as described above was cultured in a 100 mL shake flask with the medium changed daily. The expressed recombinant fusion protein reached a cumulative yield of about 30 mg/L per day. The viable cell density in the shake flask reached up to 35×10$^6$ cells/mL. The biological activities of the recombinant fusion proteins produced by the above two methods were equivalent.

Example 5. Purification and Characterization of Fusion Proteins

Affinity chromatography was mainly used in the present invention to purify FIX fusion protein F9-5B. The instrument used for protein purification in this example was AKTA Explorer 100 (GE Healthcare, USA). The reagents used in this example were all analytical-grade and purchased from Sinopharm Chemical Reagent Co., Ltd.

Step 1: affinity chromatography. Sample capture, concentration, and removal of part of contaminants were performed by using Mabselect Sure available from GE or other commercially available recombinant protein A affinity chromatography media, such as Mabselect, Mabselect Sure LX available from GE, anti-alkali Protein A Diamond available from Bestchrom, Toyopearl AF-rProteinA-650F available from TOSOH, rProtein A Bead available from Smart-Lifesciences, MabPurix available from Sepax Technologies, KANEKA KanCapA available from Pall and Eshumono A available from Merck. First, the column was equilibrated with 3-5 column volumes of equilibration buffer (20 mM PB, 140 mM NaCl, pH 6.8-7.4) at a linear flow rate of 50-100 cm/h; the clarified fermentation broth was loaded at a linear flow rate of 50-100 cm/h; after loading, the column was equilibrated with 3-5 column volumes of equilibration buffer (20 mM PB, 140 mM NaCl, pH 6.8-7.4) at a linear flow rate of 50-100 cm/h to rinse unbound components; the column was rinsed with 3-5 column volumes of decontamination buffer 1 (20 mM Citric-Citrate, 0.5 M NaCl, pH 4.8-5.2) at a linear flow rate of 50-100 cm/h to remove part of contaminants; the column was equilibrated with 3-5 column volumes of decontamination buffer 2 (20 mM Citric-Citrate, pH 4.8-5.2) at a linear flow rate of 50-100 cm/h; then the target product was eluted with elution buffer (50 mM NaAc-HAc, 1.0 M Urea, pH 3.0-4.0) at a linear flow rate of no more than 60 cm/h. Products corresponding to the target peak were collected and neutralized to neutral to acidic (pH 4.8-5.2) with 1M Tris, pH 9.0.

Step 2: anion exchange chromatography. Intermediate purification was carried out with Q Sepharase FF available from GE or other commercially available anion exchange chromatography media, such as DEAE Sepharose FF, Q Sepharose HP, Capto Q, Capto DEAE available from GE, Toyopearl GigaCap Q-650 available from TOSOH, DEAE Beads 6FF available from Smart-Lifesciences, Generik MC-Q available from Sepax Technologies, Fractogel EMD TMAE available from Merck, and Q Ceramic HyperD F available from Pall, to decrease the amount of HCP, residual DNA, and shed protein A. The eluent obtained in step 1 still contained a certain proportion of HCP, residual DNA, endotoxin and other contaminants, so it is necessary to remove these contaminants. First, the column was equilibrated with 3-5 column volumes (CVs) of equilibration buffer (40 mM $Na_2PO_4$-Citric, 0.1 M NaCl, pH 4.8-5.2) at a linear flow rate of 50-100 cm/h; the sample captured by the affinity chromatography was diluted 1 fold with the equilibration buffer and then loaded. The target protein flowed through under this condition. The flow-through samples were collected once the $A_{280}$ was raised to 100 mAU. After loading, the column was rinsed equilibration buffer (40 mM $Na_2PO_4$-Citric, 0.1 M NaCl, pH 4.8-5.2) at a linear flow rate of 50-100 cm/h, and flow-through samples were collected until the $A_{280}$ decreased to 100 mAU, at which point the collection was stopped; then the column was rinsed with 3-5 column volumes of regeneration buffer (1M NaCl, 1M NaOH) at a linear flow rate of 50-100 cm/h to regenerate the column. Samples collected were detected for HCP, DNA, Protein A, and SEC-HPLC.

Step 3, affinity chromatography. The final purification was carried out by using Cellufine Sulfate available from JNC or other commercially available affinity chromatography media such as Heparin FF and Heparin HP available from GE to remove aggregates and further remove contaminants such as HCP and DNA. First, the column was rinsed with 3-5 column volumes of equilibration buffer (20 mM PB, 100 mM NaCl, pH 7.0-7.4) at a linear flow rate of 50-100 cm/h; the target protein obtained after the anion chromatography in step 2 was diluted 1 fold with the equilibration buffer to decrease the concentration of organic matters and then loaded; after loading, the column was rinsed with 3-5 column volumes of equilibration buffer (20 mM PB, 100 mM NaCl, pH 7.0-7.4) at a linear flow rate of 50-100 cm/h; the column was then eluted with a linear gradient of salt concentrations, elution buffer: 20 mM PB, 1 M NaCl, pH 7.0-7.4, with elution buffer from 0-100%, 15 column volumes, linear flow rate of no more than 50 cm/h. The eluted fractions were collected in stages, and the collected samples were detected for protein content, SEC-HPLC, activity and HCP content respectively. The specific activity of the protein was calculated to be about 200 IU/mg as determined by protein concentration and protein activity.

Figure 3:
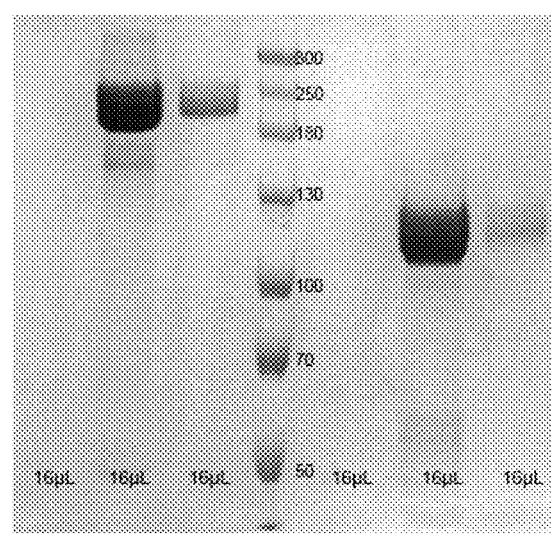
FIG. 3 shows the SDS-PAGE electrophoretogram of purified fusion protein F9-5B.

Results of the SEC-HPLC chromatography and SDS-PAGE electrophoresis of the sample are shown in FIGS. 2 and 3, respectively. The results of SEC-HPLC showed that the purity of the main peak of the purified fusion protein was more than 90%, and the band pattern in the SDS-PAGE electrophoresis was in line with expectations. The non-reduction electrophoresis contained the fusion protein, and a clear single-strand band was obtained after reduction.

Example 6. Determination of the In Vitro Activity of the Fusion Protein by a Chromogenic Substrate Assay The activity of the FIX-Fc fusion protein can be determined by a chromogenic substrate assay. In this example the BIOPHEN Factor IX kit (HYPHEN BioMed, Ref. A221802) was used for determination based on the principle as follows. Factor XIa supplied in the kit activates Factor IX presented in the tested sample into FIXa, which forms a thrombin complex with thrombin-activated FVIII:C, phospholipids (PLPs) and calcium ions ($Ca^{2+}$) in the presence of thrombin, PLPs and $Ca^{2+}$. The enzyme complex activates Factor X in the determination system into an activated form, Xa. The activation activity of the thrombin complex to Factor X is positively correlated with the content of Factor IX in the tested sample. The activity of the activated Factor Xa can be measured by its specific cleavage on a chromogenic substrate (SXa-11), that is, by measuring the absorbance of its cleavage product, pNA, at 405 nm. The absorbance of pNA is directly proportional to the activity of FIXa.

The purified FIX fusion protein F9-5B reached a specific activity of more than 200 IU/mg as determined by the present method.

Example 7 Pharmacokinetic Determination of the Fusion Protein

Male SD rats (SPF grade, purchased from Bikai Experimental Animal Co., Ltd., Shanghai) were pre-fed for 1 week and then randomly divided into 2 groups (2 rats in each group). Rats were intravenously injected with a single dose of 4.5 mg/kg (high-dose group) and 1.5 mg/kg (low-dose group) of fusion protein F9-5B respectively, and investigated for the relationship between drug concentration in blood and time. 0.3 ml of blood was collected from orbits at 0, 1, 3, 6, 24, 48, 72, 96, 120, 144 and 168 hours after administration in the control group and administration group. The blood was allowed to stand at room temperature for 30 min, and centrifuged at 5000 rpm for 10 min to isolate the serum which was then stored at −20° C. The amount of fusion protein in the serum at each time point was determined by an ELISA assay specific for FIX. The main pharmacokinetic parameters were calculated for each group by the software PKSOLVER. The results are shown in Table 2.

TABLE 2

Pharmacokinetic parameters of FIX fusion protein in SD rats

| Dose | $T_{1/2}$ (h) | AUC 0-inf_obs | Lambda_z(1/h) | Vz_obs | Cl_obs |
|---|---|---|---|---|---|
| 1.5 mg/kg | 29.89 | 25333.27 | 0.024 | 0.60 | 0.01 |
| 4.5 mg/kg | 31.57 | 80620.02 | 0.021 | 0.56 | 0.01 |

According to the pharmacokinetic data, the in vivo half-life of the high- and low-dose fusion protein F9-5B was 31 and 30 hours, respectively, which was increased by 8 times than the $T_{1/2}$ β value of rhFIX (Chinese Patent NO. CN104427994). The fusion protein F9-5B showed an improved half-life compared to rhFIX, demonstrating that the addition of a linker peptide and an Fc variant at the C-terminus of FIX did not interfere with the activity of the fusion protein, but instead produced an unexpected effect on the activity and half-life of the FIX fusion protein. It is speculated that the CTP rigid peptide, which links the FIX to a Fc variant together with a flexible peptide linker, can not only further prolong the in vivo half-life of FIX, but also increase the spatial distance between molecules in the fusion protein by means of the blocking effect resulted from multiple glycosylated side chains, which promotes FIX and the Fc segment to fold independently into correct three-dimensional conformations without affecting biological activities of each other. It can be seen that F9-5B exhibits superior performance in terms of bioavailability and pharmacokinetics compared to rhFIX.

Although preferred embodiments of the present invention have been illustrated and described, it will be understood that various changes may be made by those skilled in the art in light of the teachings herein, without departing from the scope of the invention.

All documents mentioned in the present invention are hereby incorporated by reference to the same extent as if each of the documents is individually recited for reference. It is to be understood that various modifications and changes may be made by those skilled in the art upon reading the above teachings of the present invention, which also fall within the scope of the claims appended hereto.

What is claimed is:

1. A fusion protein, wherein the fusion protein has the amino acid sequence as shown in SEQ ID NO: 8.

2. The fusion protein of claim 1, wherein the fusion protein has an activity of >200 IU/mg.

3. A DNA molecule encoding the fusion protein of claim 1, which comprises a sequence as shown in SEQ ID NO:9.

4. A pharmaceutical composition comprising a pharmaceutically acceptable carrier, excipient or diluent, and an effective amount of the fusion protein of claim 1.

5. A method for preparing a fusion protein of claim 1, comprising:
  (a) introducing the DNA sequence encoding a fusion protein of claim 1 into a CHO cell to generate a CHO-derived cell line;
  (b) screening the high-yielding cell line in step (a) which expresses more than 1 mg/$10^6$ (million) cells per 24 hours in its growth medium;
  (c) growing the cell line obtained in step (b) to express the fusion protein;
  (d) harvesting the fermentation broth obtained in step (c) and isolating and purifying the fusion protein.

6. The method of claim 5, wherein the CHO-derived cell line in step (a) is DXB-11.

7. The method of claim 5, wherein the fusion protein purification in step (d) comprises affinity chromatography and anion exchange chromatography.

8. A method for treating a hemorrhagic disease, comprising administrating a therapeutically effective amount of a fusion protein of claim 1 to a patient, wherein the patient has congenital or acquired FIX deficiency, or the patient has hemophilia B and suffers from spontaneous or surgical bleeding.

* * * * *

SEQUENCE LISTING

```
<160> NUMBER OF SEQ ID NOS: 21

<210> SEQ ID NO 1
<211> LENGTH: 415
<212> TYPE: PRT
<213> ORGANISM: Homo sapiens

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
```

```
                260                 265                 270
Leu Glu Leu Asp Glu Pro Leu Val Leu Asn Ser Tyr Val Thr Pro Ile
            275                 280                 285

Cys Ile Ala Asp Lys Glu Tyr Thr Asn Ile Phe Leu Lys Phe Gly Ser
            290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
            325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
            355                 360                 365

His Val Thr Glu Val Glu Gly Thr Ser Phe Leu Thr Gly Ile Ile Ser
            370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
            405                 410                 415

<210> SEQ ID NO 2
<211> LENGTH: 33
<212> TYPE: PRT
<213> ORGANISM: Homo sapiens

<400> SEQUENCE: 2

Pro Arg Phe Gln Asp Ser Ser Ser Lys Ala Pro Pro Pro Ser Leu
1               5                   10                  15

Pro Ser Pro Ser Arg Leu Pro Gly Pro Ser Asp Thr Pro Ile Leu Pro
            20                  25                  30

Gln

<210> SEQ ID NO 3
<211> LENGTH: 227
<212> TYPE: PRT
<213> ORGANISM: artificial sequence
<220> FEATURE:
<223> OTHER INFORMATION: Amino acid sequence of vFcgamma1

<400> SEQUENCE: 3

Asp Lys Thr His Thr Cys Pro Pro Cys Pro Ala Pro Glu Val Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
            115                 120                 125
```

```
Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 4
<211> LENGTH: 223
<212> TYPE: PRT
<213> ORGANISM: artificial sequence
<220> FEATURE:
<223> OTHER INFORMATION: Amino acid sequence of vFcgamma2-1

<400> SEQUENCE: 4

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 5
<211> LENGTH: 223
<212> TYPE: PRT
<213> ORGANISM: artificial sequence
<220> FEATURE:
```

<223> OTHER INFORMATION: Amino acid sequence of vFcgamma2-2

<400> SEQUENCE: 5

Val Glu Cys Pro Pro Cys Pro Ala Pro Val Ala Gly Pro Ser Val
1               5                   10                  15

Phe Leu Phe Pro Pro Lys Pro Lys Asp Gln Leu Met Ile Ser Arg Thr
                20                  25                  30

Pro Glu Val Thr Cys Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220

<210> SEQ ID NO 6
<211> LENGTH: 223
<212> TYPE: PRT
<213> ORGANISM: artificial sequence
<220> FEATURE:
<223> OTHER INFORMATION: Amino acid sequence of vFcgamma2-3

<400> SEQUENCE: 6

Val Glu Cys Pro Pro Cys Pro Ala Pro Val Ala Gly Pro Ser Val
1               5                   10                  15

Phe Leu Phe Pro Pro Lys Pro Lys Asp Gln Leu Met Ile Ser Arg Thr
                20                  25                  30

Pro Glu Val Thr Cys Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

```
Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220
```

<210> SEQ ID NO 7
<211> LENGTH: 229
<212> TYPE: PRT
<213> ORGANISM: artificial sequence
<220> FEATURE:
<223> OTHER INFORMATION: Amino acid sequence of vFcgamma4

<400> SEQUENCE: 7

```
Glu Ser Lys Tyr Gly Pro Pro Cys Pro Pro Cys Pro Ala Pro Glu Phe
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 8
<211> LENGTH: 739
<212> TYPE: PRT
<213> ORGANISM: artificial sequence

```
<220> FEATURE:
<223> OTHER INFORMATION: Amino acid sequence of FIX fusion protein

<400> SEQUENCE: 8

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
370                 375                 380

Ser Thr Lys Phe Thr Ile Tyr Asn Asn Met Phe Cys Ala Gly Phe His
385                 390                 395                 400
```

Glu Gly Gly Arg Asp Ser Cys Gln Gly Asp Ser Gly Pro His Val
            405                 410                 415

Thr Glu Val Glu Gly Thr Ser Phe Leu Thr Gly Ile Ile Ser Trp Gly
        420                 425                 430

Glu Glu Cys Ala Met Lys Gly Lys Tyr Gly Ile Tyr Thr Lys Val Ser
    435                 440                 445

Arg Tyr Val Asn Trp Ile Lys Glu Lys Thr Lys Leu Thr Gly Ser Gly
450                 455                 460

Gly Gly Gly Ser Gly Gly Gly Gly Ser Gly Gly Gly Gly Ser Gly Gly
465                 470                 475                 480

Gly Gly Ser Gly Gly Gly Gly Ser Ser Ser Ser Lys Ala Pro Pro
            485                 490                 495

Pro Ser Leu Pro Ser Pro Ser Arg Leu Pro Gly Pro Ser Asp Thr Pro
            500                 505                 510

Ile Leu Pro Gln Val Glu Cys Pro Pro Cys Pro Ala Pro Pro Val Ala
            515                 520                 525

Gly Pro Ser Val Phe Leu Phe Pro Pro Lys Pro Lys Asp Gln Leu Met
            530                 535                 540

Ile Ser Arg Thr Pro Glu Val Thr Cys Val Val Val Asp Val Ser His
545                 550                 555                 560

Glu Asp Pro Glu Val Gln Phe Asn Trp Tyr Val Asp Gly Val Glu Val
                565                 570                 575

His Asn Ala Lys Thr Lys Pro Arg Glu Glu Gln Phe Asn Ser Thr Phe
            580                 585                 590

Arg Val Val Ser Val Leu Thr Val His Gln Asp Trp Leu Asn Gly
            595                 600                 605

Lys Glu Tyr Lys Cys Lys Val Ser Asn Lys Gly Leu Pro Ala Ser Ile
            610                 615                 620

Glu Lys Thr Ile Ser Lys Thr Lys Gly Gln Pro Arg Glu Pro Gln Val
625                 630                 635                 640

Tyr Thr Leu Pro Pro Ser Arg Glu Glu Met Thr Lys Asn Gln Val Ser
                645                 650                 655

Leu Thr Cys Leu Val Lys Gly Phe Tyr Pro Ser Asp Ile Ala Val Glu
            660                 665                 670

Trp Glu Ser Asn Gly Gln Pro Glu Asn Asn Tyr Lys Thr Thr Pro Pro
            675                 680                 685

Met Leu Asp Ser Asp Gly Ser Phe Phe Leu Tyr Ser Lys Leu Thr Val
            690                 695                 700

Asp Lys Ser Arg Trp Gln Gln Gly Asn Val Phe Ser Cys Ser Val Leu
705                 710                 715                 720

His Glu Ala Leu His Asn His Tyr Thr Gln Lys Ser Leu Ser Leu Ser
                725                 730                 735

Pro Gly Lys

<210> SEQ ID NO 9
<211> LENGTH: 2220
<212> TYPE: DNA
<213> ORGANISM: artificial sequence
<220> FEATURE:
<223> OTHER INFORMATION: Nucleotide sequence of FIX fusion protein

<400> SEQUENCE: 9
atgcagcgcg tgaacatgat catggcagaa tcaccaggcc tcatcaccat ctgccttta      60 ggatatctac tcagtgctga atgtacagtt tttcttgatc atgaaaacgc caacaaaatt    120

```
ctgaatcggc caaagaggta taattcaggt aaattggaag agtttgttca agggaatcta      180
gagagagaat gtatggaaga aaagtgtagt tttgaagaag cacgagaagt ttttgaaaac      240
actgaaagaa caactgaatt ttggaagcag tatgttgatg gagatcagtg tgagtccaat      300
ccatgtttaa atggcggcag ttgcaaggat gacattaatt cctatgaatg ttggtgtccc      360
tttggatttg aaggaaagaa ctgtgaatta gatgtaacat gtaacattaa gaatggcaga      420
tgcgagcagt tttgtaaaaa tagtgctgat aacaaggtgg tttgctcctg tactgaggga      480
tatcgacttg cagaaaacca gaagtcctgt gaaccagcag tgccatttcc atgtggaaga      540
gtttctgttt cacaaacttc taagctcacc cgtgctgaga ctgttttttcc tgatgtggac      600 tatgtaaatt ctactgaagc tgaaaccatt ttggataaca tcactcaaag cacccaatca      660
tttaatgact tcactcgggt tgttggtgga aagatgcca aaccaggtca attcccttgg      720
caggttgttt tgaatggtaa agttgatgca ttctgtggag gctctatcgt taatgaaaaa      780
tggattgtaa ctgctgccca ctgtgttgaa actggtgtta aaattacagt tgtcgcaggt      840
gaacataata ttgaggagac agaacataca gagcaaaagc gaaatgtgat tcgaattatt      900
cctcaccaca actacaatgc agctattaat aagtacaacc atgacattgc ccttctggaa      960
ctggacgaac ccttagtgct aaacagctac gttacaccta tttgcattgc tgacaaggaa     1020
tacacgaaca tcttcctcaa atttggatct ggctatgtaa gtggctgggg aagagtcttc     1080
cacaaaggga gatcagcttt agttcttcag taccttagag ttccacttgt tgaccgagcc     1140
acatgtcttc gatctacaaa gttcaccatc tataacaaca tgttctgtgc tggcttccat     1200
gaaggaggta gagattcatg tcaaggagat agtgggggac ccatgttac tgaagtggaa     1260 gggaccagtt tcttaactgg aattattagc tggggtgaag agtgtgcaat gaaaggcaaa     1320 tatgaatat ataccaaggt gtcccggtat gtcaactgga ttaaggaaaa aacaaagctc     1380
actggatccg gtggcggtgg ctccggtgga ggcggaagcg gcggtggagg atcaggcggt     1440
ggaggtagcg gcggaggcgg tagctccagc tctagtaaag ctccccctcc ttccctgccc     1500
tcaccctcaa gactgcctgg accttccgac actcccatcc tgccacaggt ggagtgccct     1560
ccatgtccag caccccctgt cgcaggtcca tctgtgttcc tgtttccacc caagcctaaa     1620
gaccagctga tgatctcccg cacccccagaa gtcacctgtg tggtcgtgga tgtgagccat     1680
gaagaccccg aggtccagtt caattggtac gtggatggcg tcgaggtgca aacgctaag     1740 acaaaaccta gagaagagca gttcaactct acctttcgcg tcgtgagtgt gctgacagtc     1800
gtgcaccagg actggctgaa tggcaaggag tataagtgca agtgagcaa caaggactg     1860 cctgcctcaa tcgaaaagac tatttccaag accaaggac agccaagaga gccccaggtg     1920
tacaccctgc ctccaagccg cgaagagatg actaaaaatc aggtctctct gacctgtctg     1980 gtgaagggt tttatcctag tgatatcgcc gtggaatggg agtcaaacgg tcagccagag     2040
aacaattaca agaccacacc ccctatgctg gacagcgatg gtctttctt tctgtatagc     2100 aaactgacag tggacaagtc tcggtggcag cagggtaacg tcttctcttg cagtgtgctg     2160
cacgaagcac tgcacaatca ttacacccag aagtcactgt cactgagccc aggaaaatga     2220
```

<210> SEQ ID NO 10
<211> LENGTH: 16
<212> TYPE: PRT
<213> ORGANISM: artificial sequence
<220> FEATURE:
<223> OTHER INFORMATION: flexible peptide linker

```
<400> SEQUENCE: 10

Gly Ser Gly Gly Gly Ser Gly Gly Gly Ser Gly Gly Gly Ser
1               5                   10                  15

<210> SEQ ID NO 11
<211> LENGTH: 27
<212> TYPE: PRT
<213> ORGANISM: artificial sequence
<220> FEATURE:
<223> OTHER INFORMATION: flexible peptide linker

<400> SEQUENCE: 11

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 12
<211> LENGTH: 20
<212> TYPE: PRT
<213> ORGANISM: artificial sequence
<220> FEATURE:
<223> OTHER INFORMATION: flexible peptide linker

<400> SEQUENCE: 12

Gly Gly Gly Gly Ser Gly Gly Gly Gly Ser Gly Gly Gly Gly Ser Gly
1               5                   10                  15

Gly Gly Gly Ser
            20

<210> SEQ ID NO 13
<211> LENGTH: 37
<212> TYPE: PRT
<213> ORGANISM: artificial sequence
<220> FEATURE:
<223> OTHER INFORMATION: flexible peptide linker

<400> SEQUENCE: 13

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser
        35

<210> SEQ ID NO 14
<211> LENGTH: 20
<212> TYPE: PRT
<213> ORGANISM: artificial sequence
<220> FEATURE:
<223> OTHER INFORMATION: flexible peptide linker

<400> SEQUENCE: 14

Gly Gly Gly Ser Gly Gly Gly Ser Gly Gly Gly Ser Gly Gly Gly Ser
1               5                   10                  15

Gly Gly Gly Ser
            20

<210> SEQ ID NO 15
<211> LENGTH: 10
<212> TYPE: PRT
<213> ORGANISM: artificial sequence
<220> FEATURE:
<223> OTHER INFORMATION: CTP
```

<400> SEQUENCE: 15

Ser Ser Ser Ser Lys Ala Pro Pro Pro Ser
1               5                   10

<210> SEQ ID NO 16
<211> LENGTH: 14
<212> TYPE: PRT
<213> ORGANISM: artificial sequence
<220> FEATURE:
<223> OTHER INFORMATION: CTP

<400> SEQUENCE: 16

Ser Arg Leu Pro Gly Pro Ser Asp Thr Pro Ile Leu Pro Gln
1               5                   10

<210> SEQ ID NO 17
<211> LENGTH: 16
<212> TYPE: PRT
<213> ORGANISM: artificial sequence
<220> FEATURE:
<223> OTHER INFORMATION: CTP

<400> SEQUENCE: 17

Ser Ser Ser Ser Lys Ala Pro Pro Pro Ser Leu Pro Ser Pro Ser Arg
1               5                   10                  15

<210> SEQ ID NO 18
<211> LENGTH: 28
<212> TYPE: PRT
<213> ORGANISM: artificial sequence
<220> FEATURE:
<223> OTHER INFORMATION: CTP

<400> SEQUENCE: 18

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 19
<211> LENGTH: 20
<212> TYPE: PRT
<213> ORGANISM: artificial sequence
<220> FEATURE:
<223> OTHER INFORMATION: CTP

<400> SEQUENCE: 19

Ser Ser Ser Ser Lys Ala Pro Pro Pro Ser Ser Ser Ser Ser Lys Ala
1               5                   10                  15

Pro Pro Pro Ser
            20

<210> SEQ ID NO 20
<211> LENGTH: 14
<212> TYPE: PRT
<213> ORGANISM: artificial sequence
<220> FEATURE:
<223> OTHER INFORMATION: flexible peptide linker

<400> SEQUENCE: 20

Gly Ser Gly Gly Ser Gly Gly Ser Gly Gly Gly Gly Ser
1               5                   10

<210> SEQ ID NO 21

```
<211> LENGTH: 5
<212> TYPE: PRT
<213> ORGANISM: artificial sequence
<220> FEATURE:
<223> OTHER INFORMATION: flexible peptide linker

<400> SEQUENCE: 21

Gly Gly Gly Gly Ser
1               5
```